United States Patent [19]

Urmson et al.

[11] Patent Number: 5,060,507

[45] Date of Patent: Oct. 29, 1991

[54] METHOD AND APPARATUS FOR FLUID MIXTURE MONITORING, CONSTITUENT ANALYSIS, AND COMPOSITION CONTROL

[76] Inventors: John Urmson, 3807 Harrison, Oakland, Calif. 94612; Anthony Pearson, 141 Halton La., Watsonville, Calif. 95076; Sanjay Gidwani, 47112 Warm Springs Blvd., #232, Fremont, Calif. 94539

[21] Appl. No.: 369,104

[22] Filed: Jun. 21, 1989

[51] Int. Cl.⁵ ............................................. G01N 29/18
[52] U.S. Cl. .............................. 73/24.01; 73/61.1 R; 73/597; 340/632
[58] Field of Search ................. 73/24.01, 61.1 R, 579, 73/597, 861.27, 861.28; 340/603, 632

[56] References Cited

U.S. PATENT DOCUMENTS

| | | | |
|---|---|---|---|
| 2,874,564 | 2/1959 | Martin | 73/24.01 |
| 3,434,334 | 3/1969 | Vanderbussche | 73/24.01 |
| 3,468,157 | 9/1969 | Burk | 73/24.01 |
| 3,648,513 | 3/1972 | Patterson | 73/53 |
| 3,762,197 | 10/1973 | Roof | 73/24.01 |
| 3,789,655 | 2/1974 | Passeri | 73/24.01 |
| 3,892,127 | 7/1975 | Cirulis et al. | 73/61.1 R |
| 4,520,654 | 6/1985 | Terhune | 73/24.01 |
| 4,596,133 | 6/1986 | Smalling | 73/24.01 |
| 4,616,501 | 10/1986 | Mechlenburg | 73/24.01 |
| 4,630,482 | 12/1986 | Traina | 73/24.01 X |
| 4,662,212 | 5/1987 | Noguchi | 73/24.01 |
| 4,771,629 | 9/1988 | Carlson | 73/23.35 |
| 4,850,220 | 7/1989 | Asano et al. | 73/61.1 X |

FOREIGN PATENT DOCUMENTS 0233047 8/1987 European Pat. Off. ......... 73/61.1 R

OTHER PUBLICATIONS

Poulturak—"Precision Acoustic Gas Analyzer . . . ", Cited p. 8, lines 3–6, applicants' specification.
Hallewell—"A Sonar-Based Technique . . . ", Cited p. 8, lines 8–13, applicants' specification.
Faktor—"Reagent Concentration Measurements . . . ", Copy enclosed herewith.

Primary Examiner—Michael J. Tokar
Assistant Examiner—Joseph W. Roskos
Attorney, Agent, or Firm—Bruce & McCoy

[57] ABSTRACT

A method and apparatus for fluid mixture monitoring and controlling using an acoustic sensing technique by pulsing a fluid sample and a reference fluid in elongated chambers with sound waves generated at one end of the chambers and sensing the resonant frequencies in the chambers, or the time lapse for the sound waves to traverse the chambers, with transducers disposed proximate the other ends of the chambers and ratiometrically comparing the time-based measurements.

39 Claims, 8 Drawing Sheets

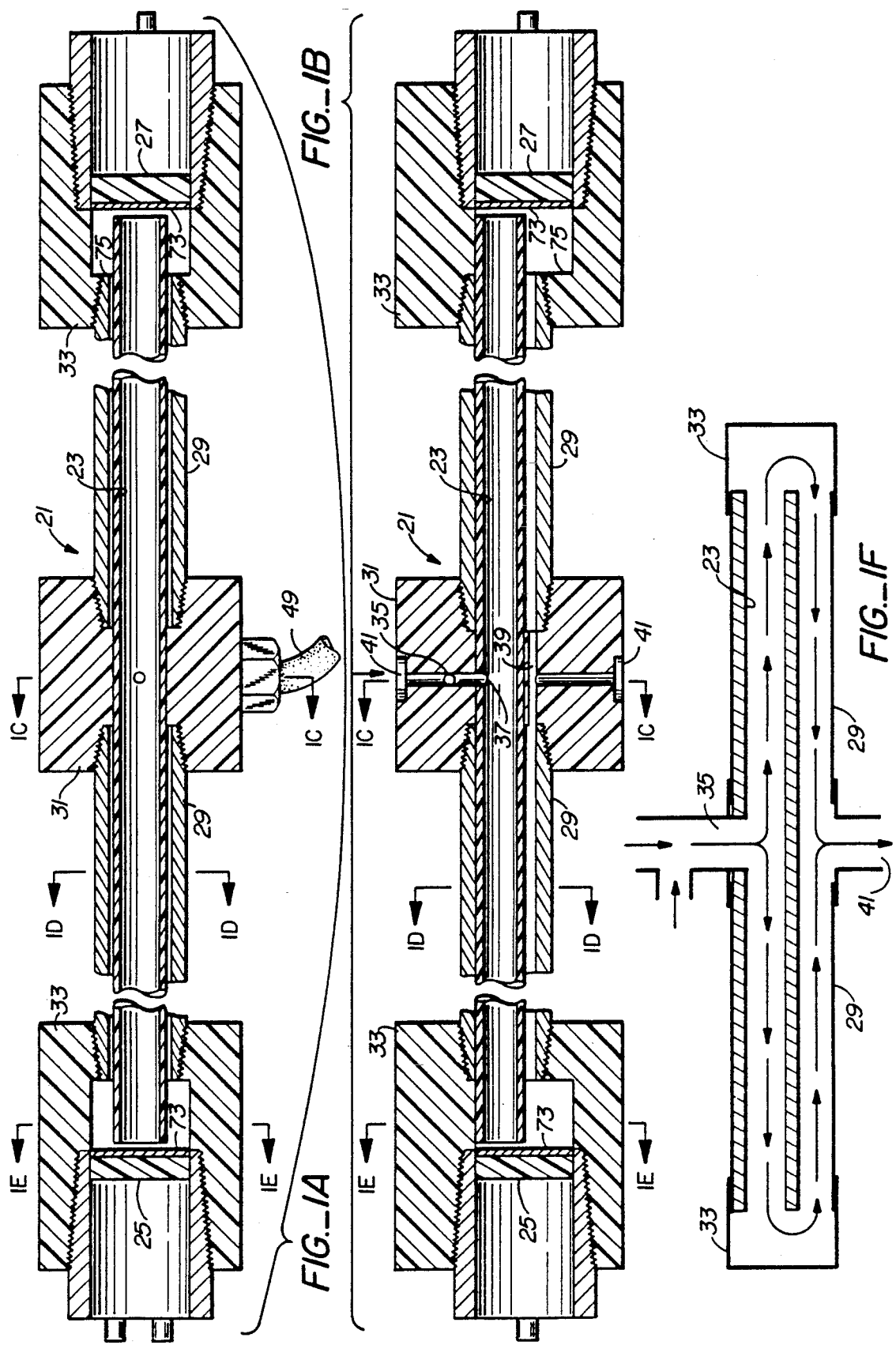

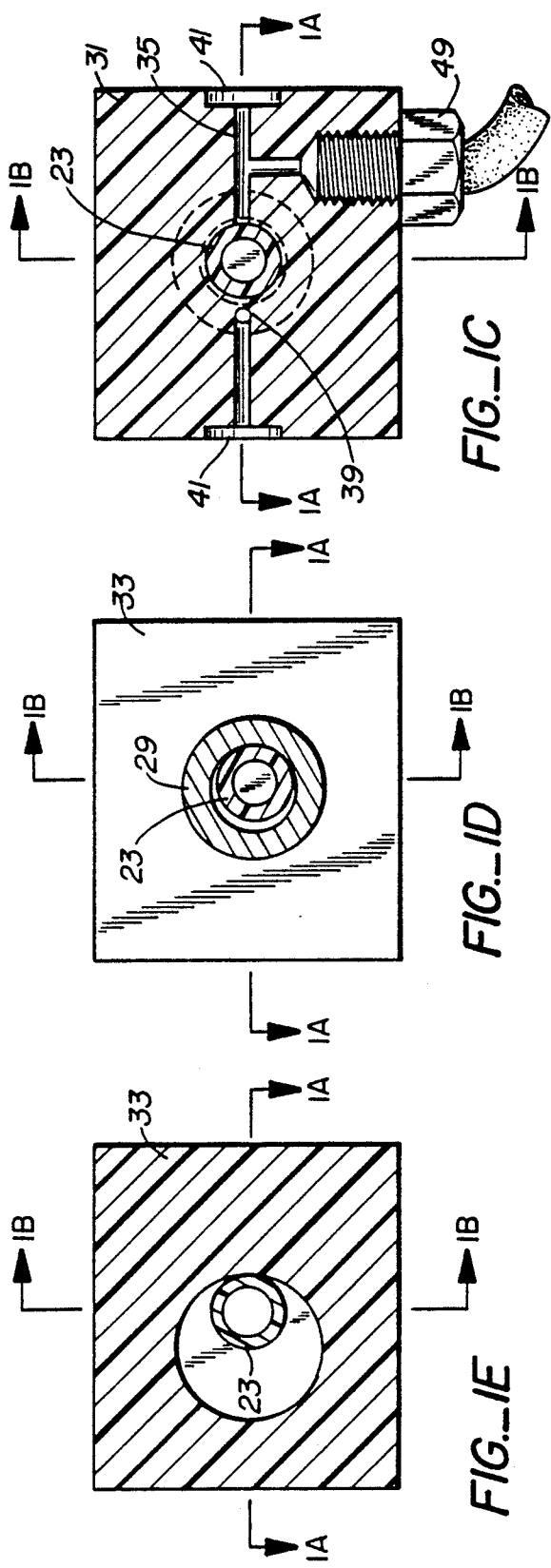

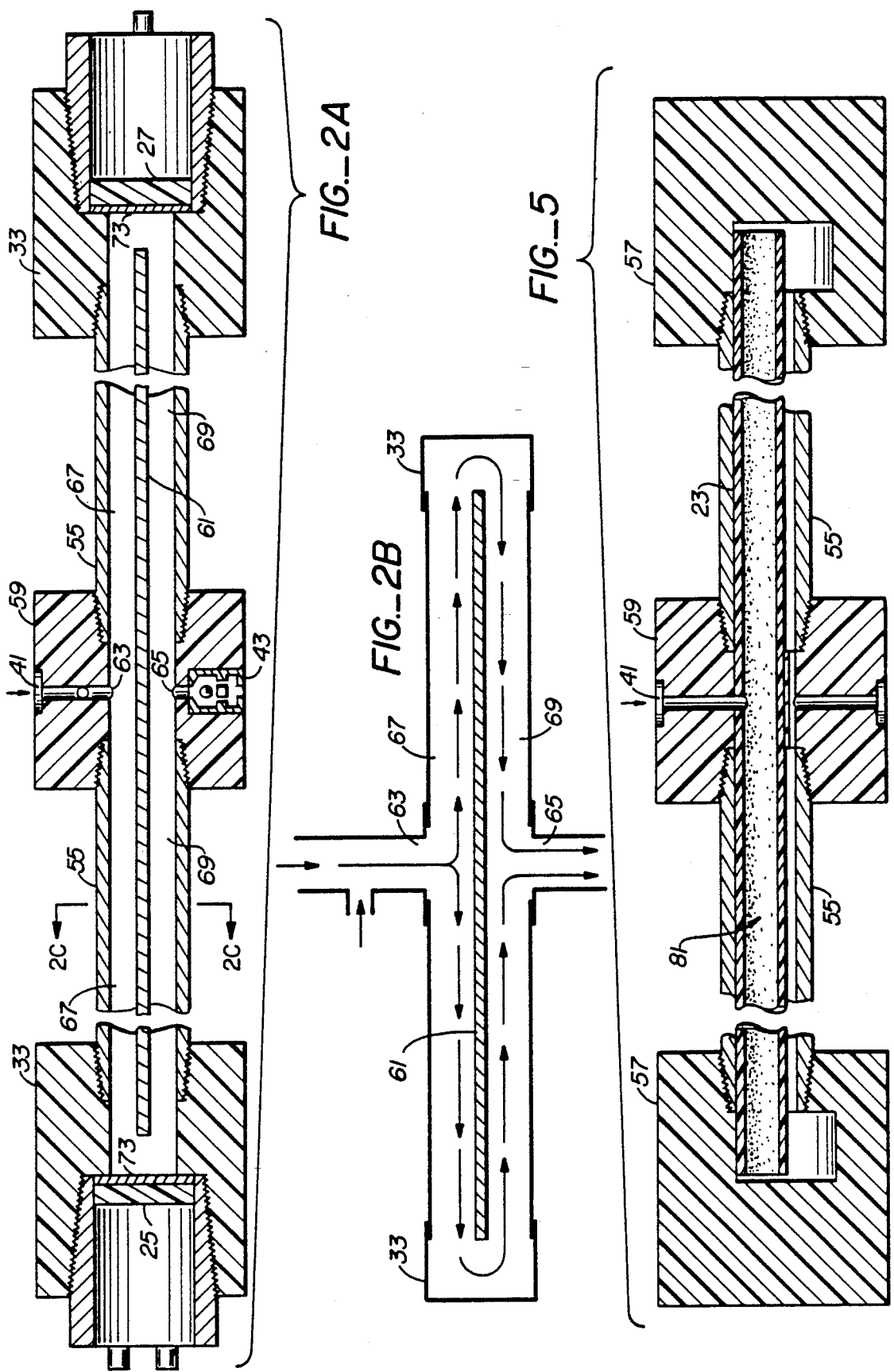

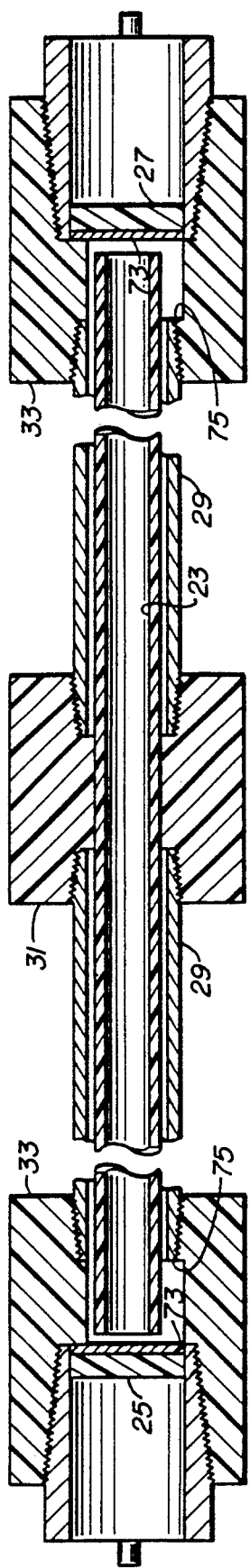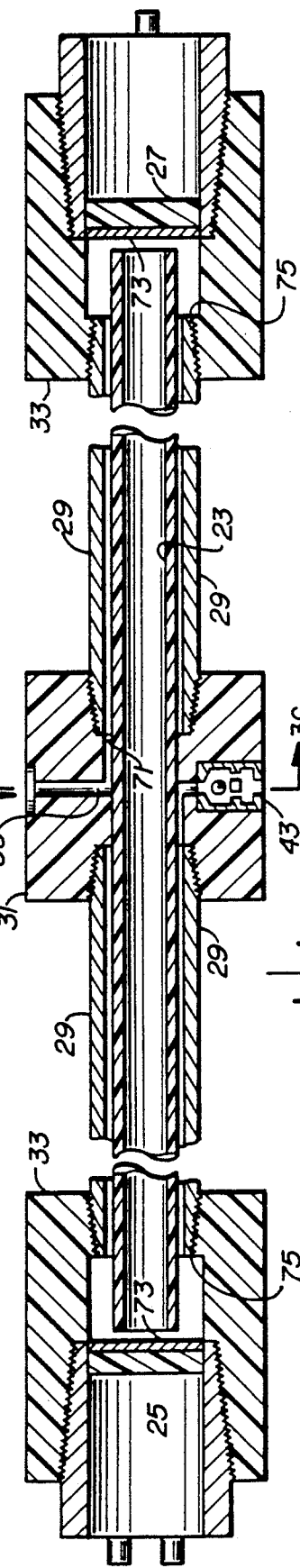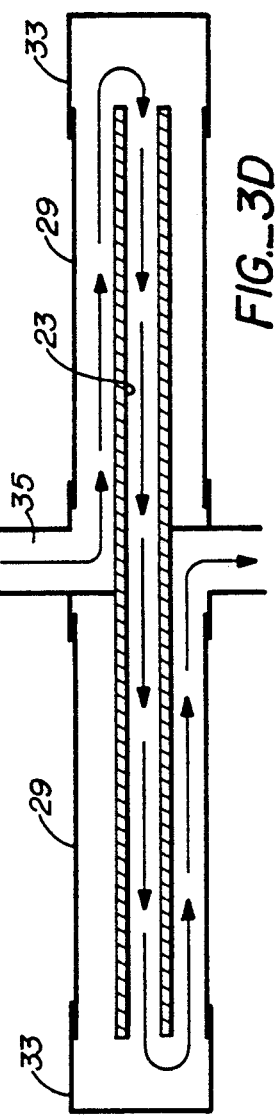
FIG._3A FIG._3B FIG._3D

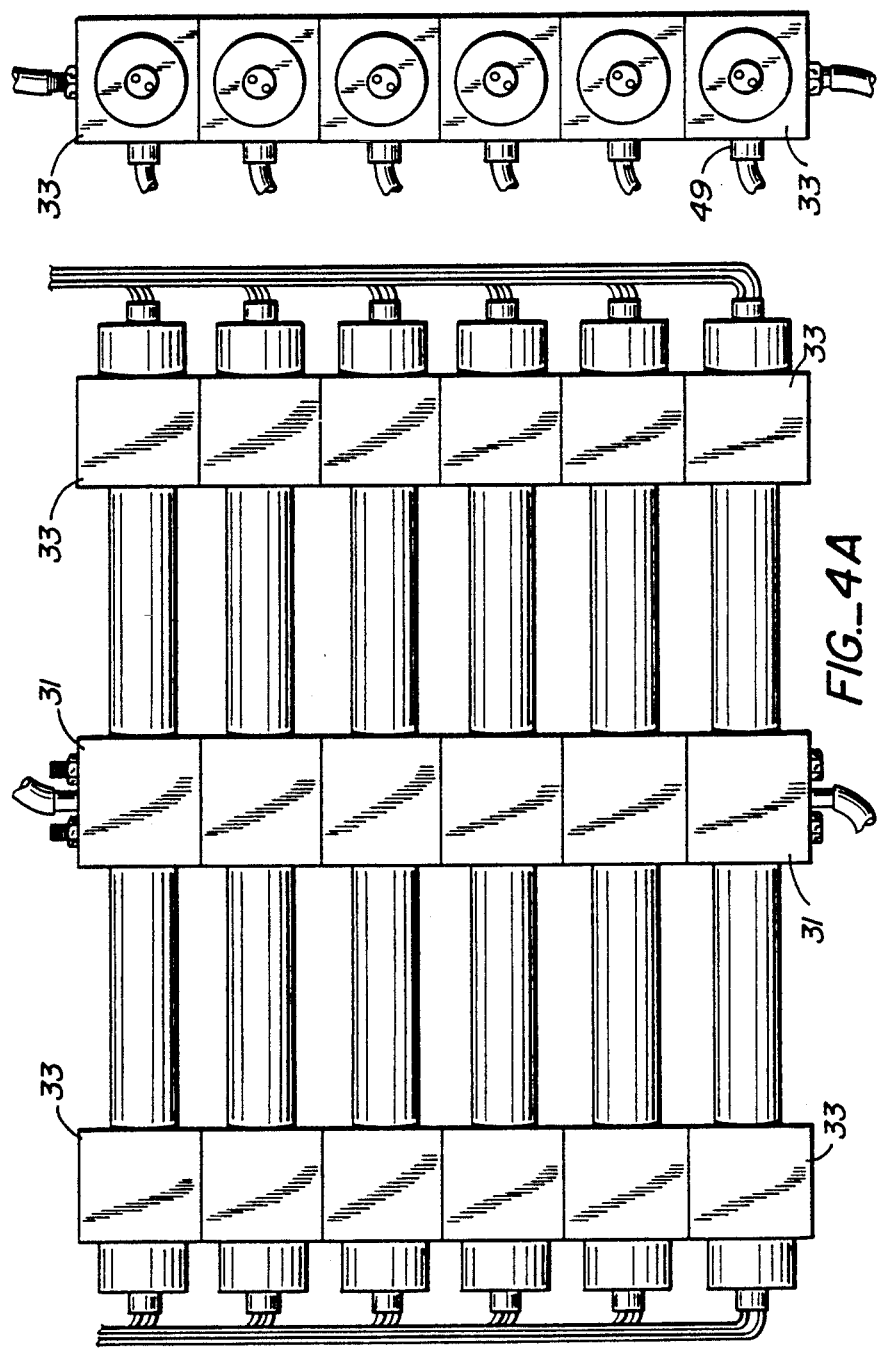

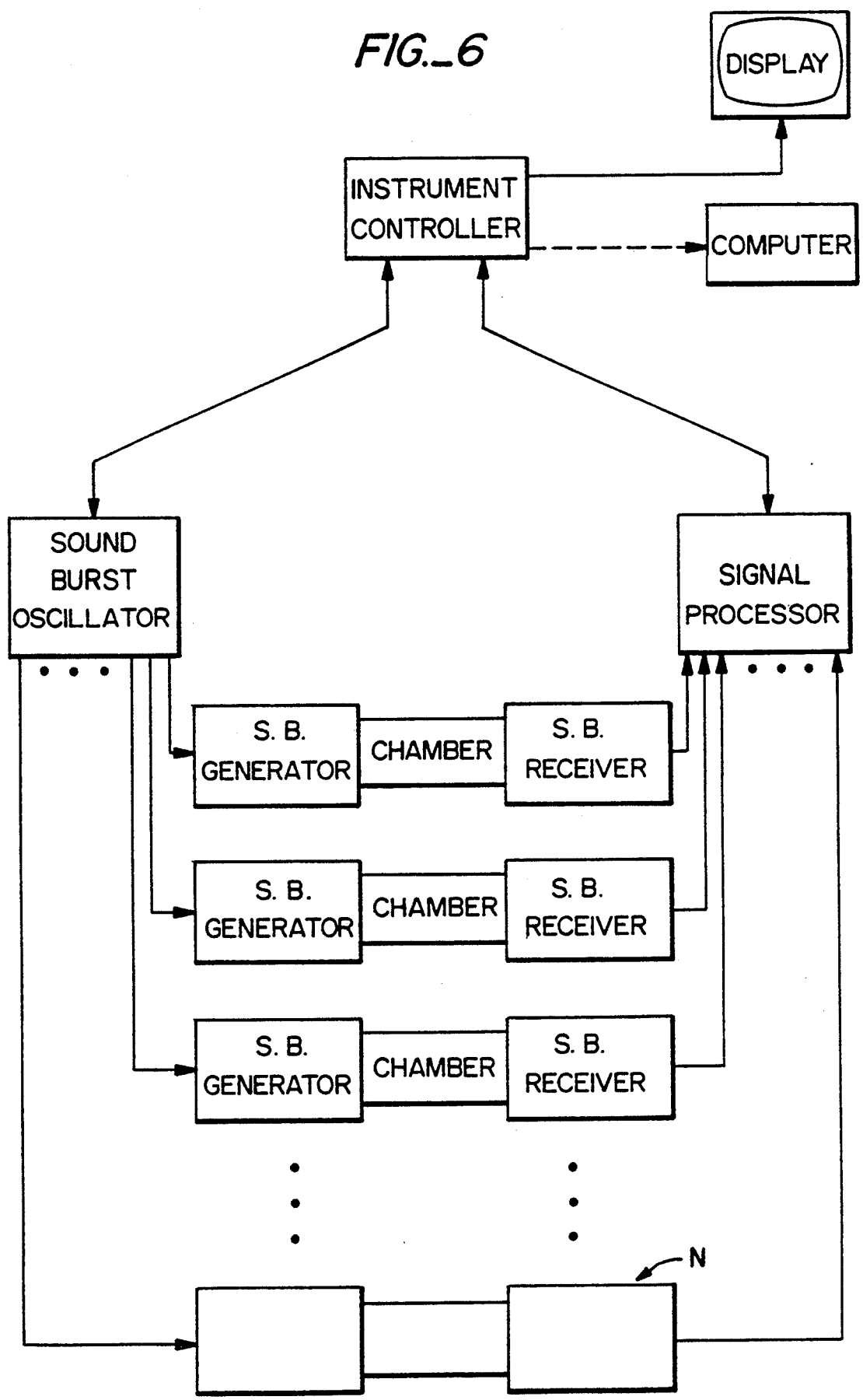
FIG._6

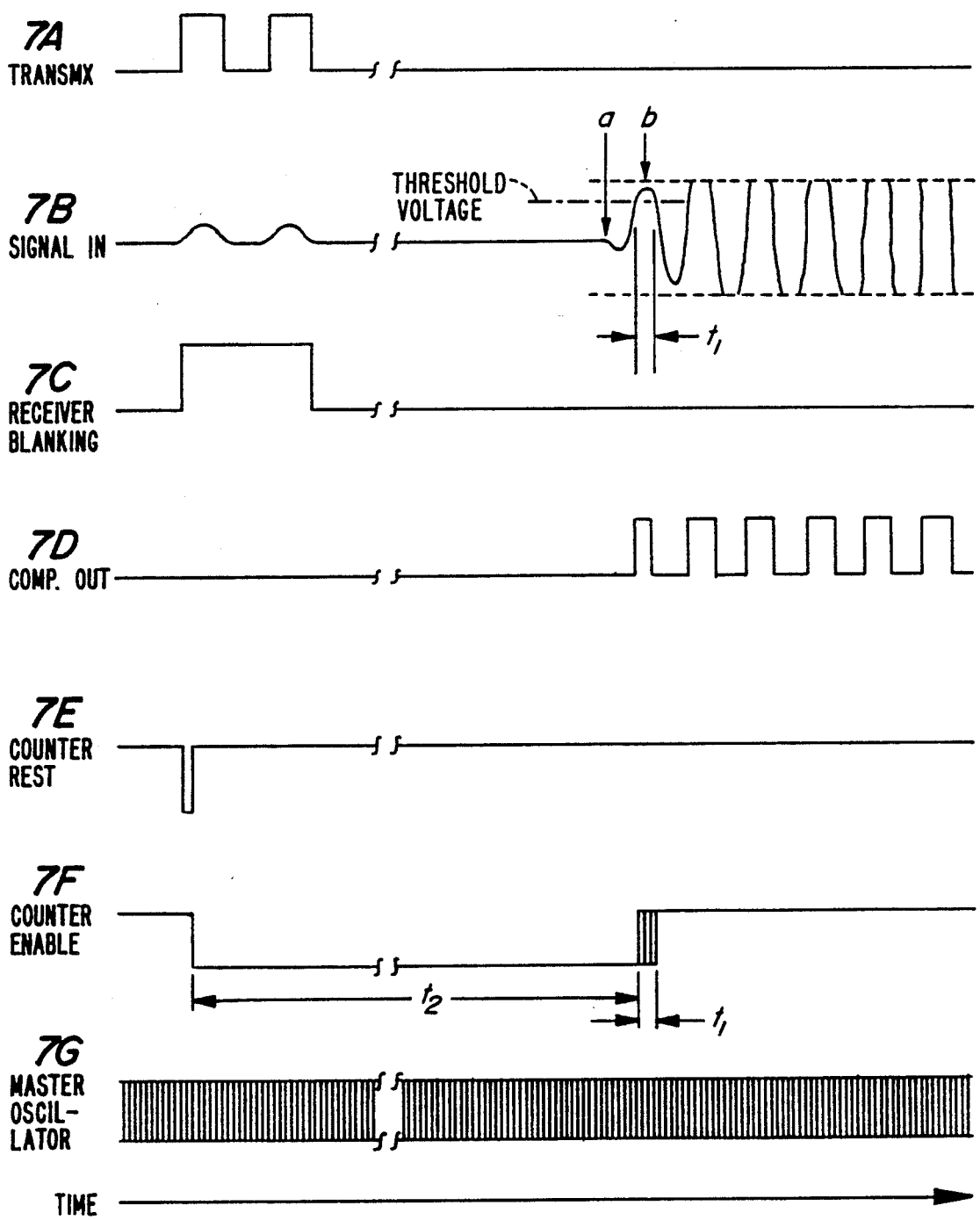
FIG._7.

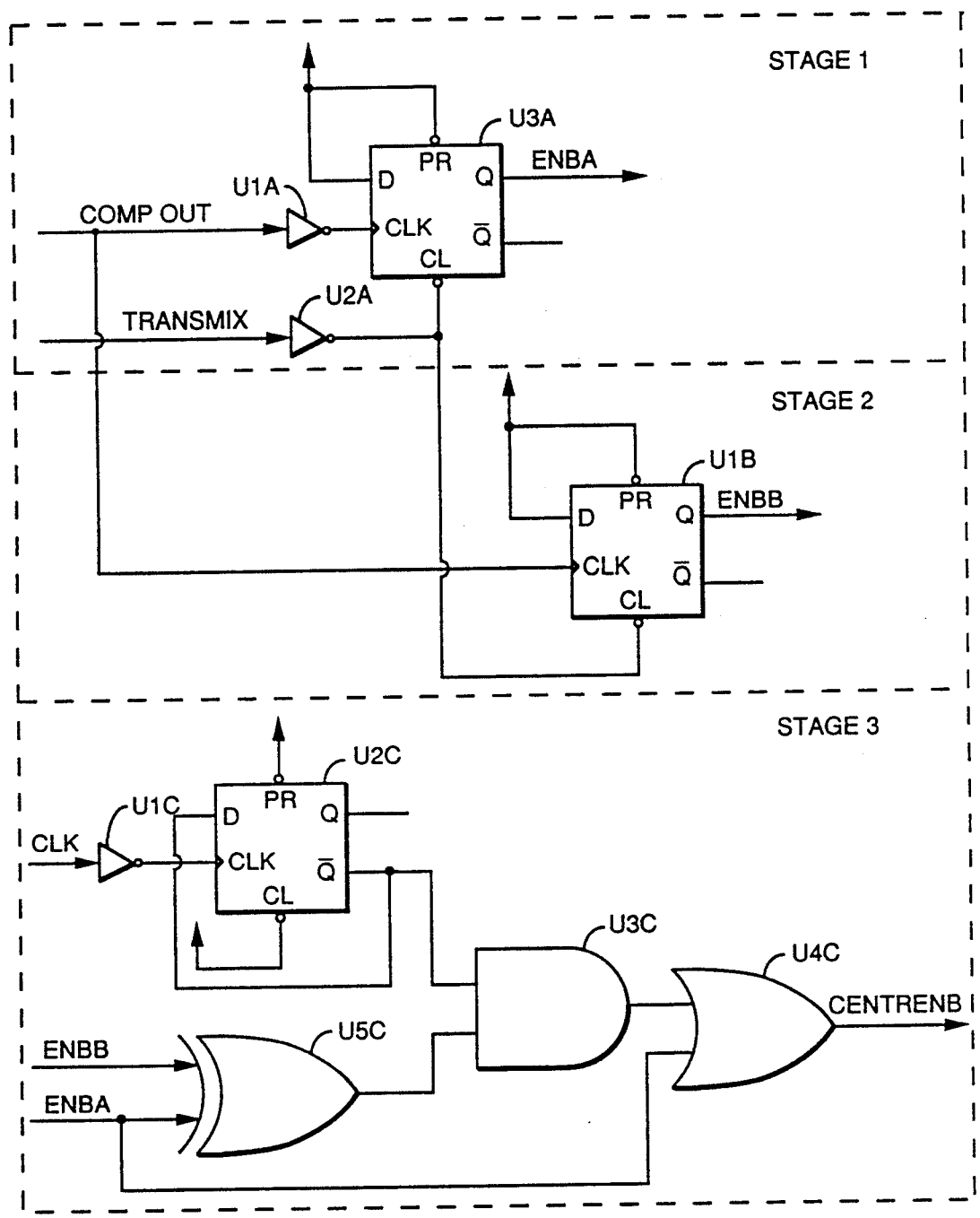
FIG._8.

METHOD AND APPARATUS FOR FLUID MIXTURE MONITORING, CONSTITUENT ANALYSIS, AND COMPOSITION CONTROL

BACKGROUND OF THE INVENTION

1. Field of the Invention

The present invention relates to methods and apparatus for monitoring and controlling the composition of fluid mixtures and more particularly to a method and apparatus utilizing nearly simultaneous measurements derived from the velocity of sound in the separate components of these fluid mixtures in a comparative sensing technique.

Some industrial processes for producing electronic devices such as chemical vapor deposition, epitaxy, reactive ion etch, and dopant diffusion require precise fluid mixtures. At present, fluid mixtures are generated by blending controlled flows of pure fluids or fluid mixtures, and the individual flows are controlled by either mechanical or electronically actuated flow regulating devices. The present invention can be used to sense the fluid compositions resulting from mixing of controlled flows of the constituent fluids, and thus to monitor the operation of said flow regulating devices.

2. Description of the Prior Art

Prior to the present invention, the best state of the art in fluid composition control was achieved through the use of mass flow controllers. While such devices represent a significant improvement over previously used fluid flow control devices, they are plagued by inherent problems. The most significant of these problems arise from the fact that the sensing of fluid mass flow is achieved by heat transfer through a metallic capillary tube which can react with the corrosive fluids involved or utilized int he processes or can become coated with foreign substances in which case the sensing devices are prone to drift in their readings. This necessitates frequent removal of the sensing devices from the processes for cleaning and re-calibration. Another major problem is that the best state of the art sensing devices achieve a precision only about 0.5% of full rated flow.

The present invention vastly improves upon these limitations. The instrument disclosed and claimed is considerably more immune to corrosion, the sensing elements never contacting the process gases. The precision obtained is on the order of 0.01% of actual fluid composition for most fluid mixtures over a much more extensive range of 0% to 100% of any fluid component of the mixture. Still another advantage derives from the fact that the sound velocity for a stable fluid is a constant value, and for this reason the disclosed instrument of the present invention is designed to respond only to sound velocity and need not be re-calibrated against a standard to correct for drift.

Another use for the present invention involves different prior art. In those processes requiring the use of low vapor pressure substances, a carrier fluid is passed over a solid or liquid source of the substance which is held at a controlled temperature so as to establish a controlled vapor pressure and, presumably, controlled mole fractions of the constituents in the carrier fluid. However, rather than relying on this technique to determine mole fractions, there is a great need to be able to measure such mole fractions directly. This is a particular problem in those processes utilizing alkylmetals, or organic forms of such substances as arsenic, cadmium, gallium, indium, mercury, phosphorous, tellurium, zinc and other substances. At the present time, researchers involved with the development of gallium arsenide and indium phosphide device technology need continuous data on the mole fractions of substances actually delivered to their reactors.

Prior to the present invention, this need for data was either unfilled or a mass spectrometer was employed for chemical constituent analysis. The mass spectrometer depends on precisely controlled conditions of temperature, magnetic flux, vacuum, and voltage in order to achieve the controlled sampling rate, molecular fragmentation, and fragment classification which are required for reproducible data. All this requires complicated machinery vulnerable to malfunction. Additionally, quantitative analysis with mass spectroscopy is an empirical technique requiring periodic re-calibration. The present invention can be used to monitor the mole fractions of low vapor pressure substances in the carrier gas directly and thus represents a vast improvement in economy and ease of operation since it is relatively inexpensive, simple, rugged, and requires no vacuum, and no re-calibration.

Yet another use for the present invention involves still different prior art. In those processes requiring highly purified gases to be delivered at a reactor vessel, great care is taken to ensure against incursion of contaminating chemicals, such as the constituents in air, as the highly purified gases are piped from compressed gas or evaporation sources to the processing chambers. Microcontamination of these processes as a result of both air incursion and particulate generation has been directly related to defects in the semiconductor devices produced in these processes, and the sources of such microcontamination must be rigorously eliminated. This is a particular problem in the production of devices of sub-micron geometry. Prior to the present invention, air incursion monitoring has been done by sample extraction followed by analysis of the high purity gas for the presence of hydrocarbons, oxygen, and water with separate analyzers. Each one of these analyzers has its own maintenance and calibration requirements, and the sample extraction itself can cause contamination. The present invention can be used to monitor for such an incursion. It can be constructed of inert materials which will not react with the process fluids. It contains no parts subject to frictional wear and produces no measurable particulate contamination in the process fluid stream. In addition, the instrument of the present invention need not be taken off line or removed for re-calibration. These attributes represent a particular advantage for use with processes which are very sensitive to microcontamination.

Still another use for the present invention involves yet different prior art. Industrial processes such as cracking, catalysis, and alkylation require that the compositions of the input and output fluid streams be monitored and/or controlled. This is routinely performed by chemical analysis employing infrared absorption, chromatography, or mass spectroscopy. Process stream analysis is usually continuous and can be supplemented with laboratory analysis. The present invention cannot replace these other techniques which perform constituent analysis, but can supplement them when used to detect changes in the composition of process streams and can thus improve the reliability of control schemes based on constituent analysis by immediately alarming when the constituency of a process stream varies beyond preset limits indicating that a process analyzer has drifted or failed. The embodiment of the present invention can, in some cases, stand in for a process analyzer while it is being repaired or recalibrated and then return to the monitoring mode.

Yet a further use of the present invention involves still different prior art. Some industrial processes require monitoring for low concentrations of contaminants such as moisture or air. The present invention can be used to detect these impurities in process streams. It is of particular use in highly corrosive process streams such as those containing halogens and their corrosive derivatives since the entire body of the instrument of the present invention can be constructed of corrosion resistant material. In addition, calibration and verification of operation in the prior art instruments, such as hygrometers, present a major problem in malevolent processes streams such as nearly pure chlorine, hydrogen chloride, or ammonia because any contaminant introduced or entering the stream quickly combines with the process chemicals or adheres to surfaces and is not available in the process stream for verification of the detection capability of the instrument. For this reason, the prior art detection instrument must be removed from the process stream and calibrated off line, then returned to the process stream and there is no verification of detection capability in the actual malevolent operating environment. The present invention, not needing re-calibration, need not be removed from the process stream. This is a significant practical advantage because the removal itself is both hazardous and can contaminate the process stream.

Still a further use for the present invention involves yet different prior art. In many industries which utilize toxic, corrosive, explosive, pyrophoric or inert gases (which if leaked into the air in sufficient quantity can cause asphyxiation by oxygen deficiency), a basic problem in the production or testing of their products is the safety of the personnel and apparatus being used in the areas where these chemicals are employed. Safety can be assured and monitored by continuously sampling the air in those environments for the presence of even minute amounts of such gases. The computer chip industry is particularly concerned because it regularly utilizes such gases in the production of its products. In these environments, a detection instrument's primary asset is reliability. Prior to the present invention, these air monitoring tasks have been performed by a variety of means such as electrochemical-based sensors, catalytic combustion-based sensors, flame photometric detectors, chemically treated paper tape based monitors, mass spectroscopy, and chromatography. While these sensing techniques have been developed to a high state of the art, they all suffer from one important disadvantage: namely, the user can never be absolutely sure they are operational. The instrument of the present invention can be used to monitor these environments; its greatest advantages being its reliability and its freedom from the requirements for frequent re-calibration and testing. The invention's use of sound which is constantly being sent and received through fluid samples provides inherent and continuous end-to-end affirmation of the detection process; a very practical means thereby to assure the device is working, and to alert operators instantaneously if it is not working.

Yet another use of the present invention involves another class of fluids: namely liquids. Liquid fluid mixtures exhibit variations in sound velocity which are dependent on the composition of the fluid. However, temperature has an unpredictable effect on sound velocity in liquid mixtures. In some liquids sound velocity increases as temperature increases and in other liquids the opposite effect is observed. It is expected that analysis of liquid samples utilizing the acoustic design principles and data handling methodology disclosed herein will prove useful in specific applications where the capabilities of presently available instrumentation is deficient; for example, monitoring of boiler feed water for sudden contamination and monitoring the concentration of dissolved substances in water used to extract sugar from sugar beets or used to blanch french fried potatoes or used to prepare syrup for soft drink and fruit canning industries.

And yet a further use for he present invention involves still different prior art. Many industrial and laboratory processes involve fermentation. For example, penicillin and other antibiotics are so produced, as are monosodium glutamate and other amino acids and acetone, ethyl alcohol and other organic chemicals. In addition, new and experimental products are so produced by recombinant organisms. Fermentation is performed in the liquid phase, but many of the essential chemicals supplied or produced are gaseous. Measurement of the gases taken up and exuded during fermentation provides a valuable tool for monitoring and control. Fermentation processes are difficult to characterize and a variety of measurements is useful, one of the most important being oxygen concentration. When oxygen or another gas is sparged through the culture medium, a mass spectrometer or a gas chromatograph is frequently employed to analyze the top gas and aid in characterizing the process. Equipped with chemical getters to selectively and sequentially eliminate specific constituents from a sample, an instrument of the present invention may be used to sample the top gas and monitor for key parameters such as carbon dioxide, methane, ammonia, and other gases of interest, thereby tracking the state of the organisms and the fermentation process. Again, an instrument of the present invention is a vast improvement over both a gas chromatograph and a mass spectrometer in terms of simplicity, reliability, and freedom from the need for re-calibration.

ACOUSTIC BASED PRIOR ART REFERENCES

In addition to constituent analysis of the composition of the gases in a fluid mixture by the previously described standard techniques, the technique of utilizing sound velocity to measure fluid flow parameters is described in U.S. Pat. No. 4,596,133 issued June 24, 1986, to James W. Smalling, and the technique of utilizing sound velocity to measure the compositions of binary mixtures has bee reported in the scientific literature. In particular, the article "(P)recision acoustic gas analyzer for binary mixtures" by E. Poulturak, S.L. Garrett, and S.G. Lipson which appeared in the November 1986 issue of *Review of Scientific Instruments* 57(11) most accurately describes the technique and a specific apparatus employed by the authors. A subsequent relevant article is "A Sonar-Based Technique For the Ratiometric Determination of Binary Gas Mixtures by G. Hallewell, G. Crawford, D. McShurley, G. Oxoby, and R. Reif published in *Nuclear Instruments and Methods in Physics Research.* A264 (1988), North-Holland Amsterdam.

However, sound velocity has not been used as a basis in any of the prior art described for air monitoring for the presence of toxic, corrosive, explosive or pyrophoric gases, or for oxygen deficiency; neither has sound velocity been used as a basis for continuous process fluid monitoring and alarming when a process fluid composition deviates from its normal constituency beyond pre-set limits; nor has it been used as a basis for process fluid composition monitoring and control. Prior to this invention, sound velocity has not been implemented as a sensing technique in an apparatus containing multiple chambers, a sequential/parallel/serial fluid flow scheme specially designed for the practical implementation of acoustic sensing technology, and a methodology for fluid composition sensing which employs comparison of time-based measurements and which renders the instrument independent from the effects of temperature and flow changes. This methodology, technique, and the essential apparatus to implement it are disclosed herein.

SUMMARY OF THE INVENTION

This invention relates to methods and apparatus for obtaining and processing time-based measurements derived from the velocities of sound in fluids. The essential aspects of this invention are: measurements in multiple fluids, using multiple acoustic analyzers or a single acoustic analyzer through which multiple fluids are flowed sequentially; and the technique for comparing these measurements for monitoring, constituent verification, composition analysis and control.

The apparatus of the present invention is a fluid mixture monitor which utilizes an elongated acoustic chamber or several such chambers herein designated acoustic analyzers. A means is provided for generating a sound wave at one end of the analyzers in response to electrical impulses. Receiving transducers are disposed proximate to the other ends of the analyzers approximately equidistant from said sound wave generators for converting sound waves in said acoustic analyzers into electrical impulses to permit measurement of time-of-flight of the sound waves or the resonant frequency in the analyzer chamber.

The present invention includes improvements in apparatus design, innovative use of said apparatus, and a unique methodology for processing data. It utilizes time or frequency (reciprocal time) measurements which are derived from the sound velocity of the fluid(s) in the analyzer chamber(s). The two most common ways of obtaining such measurements, time-of-flight and acoustic resonance, are described in detail in the referenced prior art. (An earlier method known as "sing around," occasionally mentioned in references, is related to time-of-flight and was replaced by the latter as electronic timing circuitry became more precise.) The present invention can utilize either methodology.

Acoustic resonance involves circuitry which automatically tunes the frequency of the sound in a resonating chamber to maximize sound amplitude, said frequency being dependent on sound velocity in the fluid in the chamber. A simple implementation is based on the use of an analog phase locked loop controller for frequency tuning and a frequency to voltage converter for converting said frequency to an analog signal, both of which are standard items of commerce and available as integrated circuit chips. This measurement technique provides time-based (frequency) data with a "Q" multiplex advantage where the value of "Q" is that of the resonating chamber. While the embodiment is simple and inexpensive to produce, it has disadvantages which derive from the impracticality of producing the very small chambers wherein fundamental resonant frequencies for gaseous fluids are in the ultrasonic range and wherein the values of "Q" are sufficiently high for the level of precision needed for many monitoring and control purposes. A further disadvantage is the possibility of "mode-hopping" or tuning to a different harmonic when frequencies higher than the fundamental resonant frequency are utilized. "Mode-hopping" can occur when fluid mixture compositions change rapidly. Conventional analog circuitry cannot identify this event and correct the data. These phenomena are well explained in the referenced literature.

Time-of-flight is a technique which lends itself more easily to digital implementation and yields time-based measurement data. These digital data are readily processed by computer to maximize data quality as disclosed later herein. This technique may be practically implemented in the ultrasonic frequency range with high "Q" transducers (as opposed to broad band low "Q" transducers required for the acoustic resonance measurement technique), rendering the instrument less susceptible to the effects of background acoustic noise. The additional expense of digital implementation and computing becomes less significant in a multi-analyzer instrument with measurement interlacing as disclosed later herein. In addition, the time-of-flight technique may be used to measure fluid flow rate when the fluid flow path is altered, as disclosed later herein.

The preferred embodiment described herein employs the time-of-flight measurements. However, the design principles and comparative sensing method disclosed are applicable to either measurement methodology, and apparatus to utilize acoustic resonance measurements differs only slightly from that described herein. Instruments of the present invention contemplate either measurement methodology, depending on the requirements of the intended use of said instruments.

The steps in the measurement process comprise first introduction of a fluid, here designated "reference," into one acoustic analyzer and a fluid here designated "sample" into a second acoustic analyzer, with both fluids at the same temperature. Second, sound waves are generated at one end of the analyzers in response to electrical impulses. The analyzers are monitored at the opposite ends thereof from the sound wave generating sources with sound wave sensors which are spaced approximately equidistant from said generating sources and produce electrical impulses in response to the sound waves. Third, the time lapses between the electrical impulses which generate sound waves in the reference fluid and the sample fluid and the electrical impulse produced by the sound wave sensors in response thereto are measured and the time lapse for the sample is compared ratiometrically with the time lapse for the reference fluid. Fourth, the results of said comparison are compared to set-points for control and alarming purposes and actuation of output devices such as meters, relays, etc. It is to be noted that the above description is based on the use of two analyzers, and that the measurement technique of ratiometric comparison of measurements dependent on sound velocities disclosed here is not limited to the use of two analyzers, but may be utilized with one or many analyzers operating as a single instrument. Where a single analyzer is used, fluid samples are switched externally so as to flow through the analyzer sequentially.

OBJECTS OF THE INVENTION

It is therefore an important object of the present invention to provide a new and novel sensor apparatus which can be used to continuously monitor deviations in the composition of a fluid mixture by referral to a reference fluid mixture.

It is another object of the present invention to provide a new and novel method for sensing the presence of unwanted gases present in an air sample.

It is a further object of the present invention to provide a new and novel method for sensing the presence of low concentrations of contaminating fluids in process fluid streams.

It is still another object of the present invention to provide a new and novel sensor apparatus which can be used for the purpose of monitoring the accuracy of separate flow regulating devices where individual flowing fluids are being mixed in order to attain a desired composition.

It is yet another object of the present invention to provide a new and novel sensor apparatus which can be used to sense fluid composition and to control the flows of the individual fluids being mixed in order to attain a desired composition.

It is still a further object of the present invention to provide a new and novel sensor apparatus which can store fluid mixture receipes in electronic memory and utilize said receipes to indicate deviation in the amounts of the individual mixture components comprising the entire mixture.

It is yet a further object of the present invention to provide a new and novel sensor apparatus which can be used to check and identify individual fluids before they are mixed in order to assure that the correct fluids are utilized for the mixing operation.

It is still yet another object of the present invention to provide a new and novel sensor apparatus which can be used to measure fluid flow.

It is still yet a further object of the present invention to provide new and novel sensor apparatus which can be used to sense the composition of gas mixtures by selectively gettering or eliminating specific components of the mixture.

And it is still another object of the present invention to provide a new and novel sensor apparatus wherein the sensing technique is not subject to drift and wherein systematic instrument errors do not exist and where fluid mixture receipes are transferable between individual instruments.

Other objects and advantages of the present invention will become apparent when the method and apparatus of the present invention are considered in conjunction with the accompanying drawings.

DESCRIPTION OF THE DRAWINGS

FIG. 1A is a front elevation in cross-section of the apparatus of the time-of-flight sonic analyzer of the present invention;

FIG. 1B is a top plan view in cross-section of the sonic analyzer of FIG. 1A;

FIG. 1C is a cross-section taken along lines 1C—1C of FIGS. 1A and 1B;

FIG. 1D is a cross-section taken along lines 1D—1D of FIGS. 1A and 1B;

FIG. 1E is a cross-section taken along lines 1E—1E of FIGS. 1A and 1B;

FIG. 1F is schematic flow diagram for the fluid flow through the time-of-flight sonic analyzer of FIGS. 1A and 1B;

FIG. 2A is a front elevation in cross-section of the apparatus of the acoustic resonance sonic analyzer of the present invention;

FIG. 2B is the schematic flow diagram for the fluid flow through the acoustic resonance sonic analyzer of FIG. 2A;

FIG. 2C is a cross-section taken along lines 2C—2C in FIG. 2A;

FIG. 3A is a front elevation in cross-section of the apparatus of the fluid flow measurement sonic analyzer of the present invention;

FIG. 3B is a top plan view in cross-section of the sonic analyzer of FIG. 3A;

FIG. 3C is a cross-section taken along lines 3C—3C in FIGS. 3A and 3B;

FIG. 3D is the schematic flow diagram for the fluid flow through the fluid flow measurement sonic analyzer of FIGS. 3A and 3B;

FIG. 4A is a top plan view of an array of sonic analyzers without their enclosure;

FIG. 4B is a side elevation of the array of sonic analyzers of FIG. 4A;

FIG. 4C is an end view of the array of sonic analyzers of FIG. 4A;

FIG. 5 is a front elevation in cross-section of the apparatus of a gettering section of the analyzer train;

FIG. 6 is a block diagram of the assembly of hardware comprising the apparatus of the present invention;

FIG. 7 is a time diagram for the detector logic circuitry; and

FIG. 8 is a circuit logic diagram for the clock enable circuitry of a preferred embodiment of the present invention.

DESCRIPTION OF THE PREFERRED EMBODIMENT

Reference is made to the drawings for a description of the preferred embodiment of the present invention wherein like reference numbers represent like elements on corresponding views.

FIGS. 1A-1E illustrate a preferred embodiment of a basic element of the invention. There shown is an acoustic analyzer 21 which is an acoustic chamber containing a sound wave guide tube 23 where the time-based measurements derived from the velocity of sound in a fluid are obtained. The analyzer is used for analyzing fluid mixtures by creating sound waves in the fluids to be tested which are introduced into the guide tube. A sound burst generator 25 creates the sound waves which are sensed by a sound burst receiver 27. The acoustic analyzer of &:he present invention contemplates alternative embodiments wherein the sound burst generator and receiver can be the same unit disposed at one end of the acoustic chamber. In that embodiment, the unit is programmed to switch and alternate and both generate and receive the sound burst which is reflected off the other end of the chamber. In the preferred embodiment, the sound burst generator and receiver are separate units and are disposed at opposite ends of the acoustic chamber.

A special means is provided for introducing a fluid sample into the acoustic chambers. An important aspect of the this fluid introduction means is that it has been designed so as to assure that all fluids are introduced into the chambers at the same temperature. This is important because sound velocity in any fluid varies with temperature and the method of the present invention employed for interpreting sound velocities to yield useful monitoring and control information, described later herein, is based on the premise that all fluids are at the same temperature.

ACOUSTIC ANALYZER TRAIN

An instrument of the present invention may contain one acoustic analyzer used alternatively for the sample fluid and the reference fluid, or it may include several acoustic analyzers.

Fluid constituent analysis is achieved by measuring the effect of each constituent as it is added to the mixture. Several analyzers may be connected together to comprise a single instrument to accomplish constituent analysis. When so connected, the individual analyzers are arranged and secured in mutually abutting contact and means are provided for leak-proof fluid connections between the analyzers. This allows sample fluid from one analyzer to be exhausted into one of the inlets of the next analyzer where it is mixed with another fluid component resulting in serial addition and mixing of individual fluid components. Acoustic analyzers connected in this manner form an "analyzer train."

Constituent analysis may also be performed by utilizing gettering or selective scrubbing of specific fluid components from the fluid mixture and measuring the effect. To achieve this result, special "gettering sections" illustrated in FIG. 5 are installed between acoustic analyzers. These gettering sections are constructed using the same structure and fluid connections as acoustic analyzers except that the chambers contain no sound burst generator and receiver assemblies, no inlet for another fluid addition, and the chamber includes an appropriate chemical system for the desired gettering action (for example, potassium hydroxide to getter carbon dioxide). The result is sample flow from one acoustic analyzer to a gettering chamber, through the chemical gettering system, and out of the gettering chamber and into the next acoustic analyzer.

THE TEST CHAMBER AND SOUND WAVE GUIDE TUBE

The acoustic chamber of the preferred embodiment of the invention includes the sound wave guide tube 23 which is enclosed within a pair of corrosion resistant containment or sample return tubes 29. These are sealed to a manifold or center block 31 disposed at the center of the guide tube. The containment tubes could be made of glass but for strength and safety are made of stainless steel. The ends of the tubes are sealed by sound attenuating end blocks 33 made of corrosion resistant material. Both the end blocks and the guide tube are made of a chemically inert generally mechanically rigid material having a complex molecular structure for converting sound energy in the material into heat so that sound energy in the material is strongly attenuated. This is so the end blocks and the guide tube do not function as acoustic conductors.

THE FLUID INTRODUCTION MEANS

In the preferred embodiment of the invention, the fluid introduction means comprises the center block 31 of the acoustic chamber which is machined from a corrosion resistant relatively high heat transfer material such as stainless steel. Reference is made to FIGS. 5, 6 and 7. The central block includes machined manifolding, or internal ducting, for directing the incoming fluid flow and for ingesting the return flow from the sample return tubes 29. The incoming fluid flow is routed through an inlet channel 35 in the center block and ducted to an orifice 37 formed to discharge the fluid flow into the center of the guide tube 23 where it bifurcates and flows toward the opposite ends of the guide tube. The fluid flow exits both ends of the guide tube, then reverses direction at the ends of the chamber and flows outside the guide tube 23, but inside the containment tubes 29 of the chamber, back to the central block 31. There it is ingested by the central block and directed to the exit port 39 for expelling it either back into the process stream or into the next chamber depending upon the use of the instrument.

The guide tube 23 is inserted through a bore in the central block 31 with a slight friction fit so that it is essentially sealed in the bore with both ends projecting equidistant from the central block. After the guide tube is disposed in position, a hole is drilled in the guide tube 23 through the central block inlet channel 35 forming the inlet port 37 and providing a fluid passageway which connects the guide tube to the central block. The alignment of the inlet channel 35 with the inlet port 37 assures that all the sample fluid flows directly into the center of the guide tube where it divides equally and flows to the opposite ends of the guide tube. The opposite directions of fluid flow within the guide tube is the special feature of the fluid flow introduction means which eliminates measurement anomalies due to the Doppler effect. The fluid flow path is illustrated in FIG. 1F.

In a multiple chamber instrument, the center blocks 31 are formed for abutting contact to permit fluids to flow from one center block to the next through the internal manifolding formed in part by the inlet and outlet channels 35 and 39. The ends of the channels, at the surface of the center blocks, are provided with recesses 41 for inclusion of an "0" ring seal which can be disposed between the adjacent center blocks to seal the passageways which communicate between the adjacent center blocks.

Reference is made to FIGS. 3C and 4A which illustrate that the center blocks can be further provided with check valves 43 which prevent fluid mixing in the direction opposite the fluid flow when very low flow rates are encountered. Any one of several commercially available types will serve the purpose. Each block is also provided with the capacity to provide for machining a control valve seat 45 into the material by drilling the inlet channel 35 to the analyzer. The inlet channel is comprised of two tributaries: an inlet receiving fluid from an adjacent preceding analyzer in a train of analyzers and a separate inlet from an outside source. A modulating valve topworks 47 is then installed into the valve seat, and the solenoid of the valve or other type actuator is connected to a control signal which is generated by the instrument controller.

Fluids may enter the center block through the two inlet tributaries through that portion of the inlet channel 35 which mates with the outlet orifice of an adjacent center block of another acoustic chamber and from an outside source through a supply tube 49 connection to the check valve 43 on the bottom of the center block 31. Valve seats can be provided at both of the inlets to the center block to allow fluid to selectively enter the chamber through either one or both of the tributary inlets. Incoming fluids from the two inlets are mixed and adjusted to the temperature of the center block, which may be at ambient or an elevated temperature, as a result of containment therein and contact therewith. The temperature-adjusted fluid mixture is thereafter fed into the middle of the guide tube 23 where it flows to either end.

Another important aspect of said fluid introduction means is that it has been designed so as to permit either serial, parallel, or sequential addition of fluids, and when serial introduction is employed, it provides for fluid mixing outside the chambers so as to eliminate sound velocity measurement errors resulting from incomplete mixing of fluids within the chamber. Both of these purposes are accomplished by the design which includes a pre-chamber into which fluids are introduced, mixed, and adjusted in temperature to that of the surrounding enclosure prior to flowing into the chambers. The prechamber is that portion of the inlet channel 35 between the intersection of the inlet tributaries and the orifice 37 which discharges the mixed fluids into the sound wave guide tube.

Still another important aspect of the fluid introduction means is its elimination of measurable effects on the sound velocity measurements of varying fluid flow rates encountered in normal operating conditions, which are typically 0.2 to 2 liters per minute for each fluid. The fluid is inletted at the center of the guide tube and caused to flow to both ends whereby the sound waves traverse equal amounts of opposite direction fluid flow. This flow path results in a canceling of both the Doppler shift and acoustic wave pulse distortion which can occur as a result of fluids flowing within a tube, and allow for precise sound velocity measurements throughout the laminar and transition flow regimes, or where Reynolds numbers can vary between zero and approximately 3,000. Said flow path further provides for the sound transmitter and receiver to be located at opposite ends of the acoustic analyzer, or for a single transmitter/receiver to be located at one end and a sound reflector located at the opposite end of said acoustic analyzer.

ACOUSTIC RESONANCE MEASUREMENT APPARATUS

When acoustic resonance is used as a means to obtain sound velocity based measurements, the construction details of the acoustic analyzer are modified to accommodate this technique. Reference is made to FIG. 2A for an illustration of this embodiment of the apparatus of the present invention. Containment tubes 55 are utilized which are of the same internal diameter as the bore of the end blocks 57. The center block 59 is drilled through along the axis of the containment tubes with a bore of the same diameter as the internal diameter of the containment tubes so that a chamber is formed in the containment tubes of uniform diameter when the acoustic analyzer is assembled. A septum 61 in the form of a strip of suitable material (generally rigid and inert) is then pressed lengthwise into this chamber between the inlet and outlet orifices 63, 65 for sample in-flow and out-flow on opposite sides of the septum. It forms a wall in the analyzer which creates two chambers. A slight friction fit is generally sufficient for securing the septum in the containment tubes. The length of the septum is slightly less than the distance between the transducers disposed at the ends of the chambers in the end blocks so as to allow for the fluid sample to flow around the ends of the septum from the inlet to the outlet. This results in the formation of two fluid flow cavities within the analyzer resonating chamber.

Reference is made to FIG. 2B for an illustration of the fluid flow path in an acoustic resonance sonic analyzer. Sample fluid flows into the first cavity 67 on one side of the septum 61 and bifurcates and flows toward opposite ends of the cavity into the end blocks 57. It then reverses direction and enters the second cavity 69 and flows from either end toward the center block 59 where it is ingested into the exit orifice 65 and is expelled into the process or into the center block of the next acoustic analyzer in the analyzer train. The result is sample flow through the two cavities formed in the resonating chamber of the acoustic analyzer on opposite sides of the septum such that generated sound waves encounter equal distances of opposite directions of sample flow.

FLUID FLOW MEASUREMENT APPARATUS

Another important aspect of the fluid introduction means is the provision for directing the fluid flow in a sound wave guide tube in a single direction and thereby permitting the measurement of fluid flow. Reference is made to FIGS. 3A and 3B for an illustration of this embodiment of the apparatus of the present invention. In this configuration, the inlet tube 49 for new fluid introduction is plugged or valved off and no fluid is added to the fluid flow from the previous acoustic analyzer in the analyzer train so that fluid of identical composition to that in the previous acoustic analyzer is flowed through the acoustic analyzer which is arranged for flow measurement. The sample inlet channel 35 to the center of the guide tube is routed through a channel 71 in the center block 31 to a containment tube 55 on one side of the center block. There is no channel provided for return sample flow ingestion into the center block on that side of the center block resulting in a flow of sample from the center block through one containment tube to the (right) end block to which it is attached, then into the guide tube and out the other (left) end of said guide tube and into the other end block, then into the other containment tube where it flows back (right) into the center block where it is ingested and discharged as with the other analyzers.

This fluid flow path results in sound waves transmitted through the guide tube encountering fluid flow in only one direction when a separate sound burst generator 25 and sound burst receiver 27 are employed and disposed proximate to opposite ends of said guide tube 23. Fluid flow is computed from the sound and flow velocity dependent measurements obtained. This process is disclosed in detail later herein, in "Method of Operation," section 6.

THE SOUND BURST GENERATOR AND RECEIVER

Reference is made to FIGS. 1A, 1B, 2, 3A and 3B. A means is provided for generating a sound wave at one end of the sonic analyzer in response to electrical impulses. This is effected by the sound burst generator 25 which includes a transducer. In the preferred embodiment of the invention, a sound burst receiver 27 is disposed proximate of other end of said chamber. The sound burst receiver also includes a transducer. The sound burst receivers are disposed approximately equidistant from said sound wave generators for converting the generated sound waves in said chambers into electrical impulses. The transducers are mounted proximate to the ends of the stainless steel containment tubes 29, 55 by means of end blocks 33, 57 which screw onto the containment tubes and acoustically couple to fluids in the guide tubes 23 by means of metal diaphragms 73. The diaphragms may be coated with gold, tantalum, glass or otherwise passivated for use with corrosive fluids. The diaphragms isolate the transducers from the acoustic chambers whereby the transducers are disposed outside of the chamber for reliability and to isolate the tested fluid from the transducing elements, the associated electronic components, and the outside environment, preventing possible leakage or contamination of the fluids.

TEST CHAMBER PARAMETERS, MATERIALS, AND CONSTRUCTION

Reference is made to FIGS. 1A and 1B illustrating the time-of-flight preferred embodiment of the sonic analyzer of the present invention. The cavity within the end block assembly 33 is cylindrical, with one end formed by the transducer diaphragm 73 and the opposite end formed by the internal wall 75 of the end block. Acoustic reflections between these two surfaces distort the received waveforms and cause sound velocity measurement errors. Means are provided for eliminating these reflections and thereby eliminating the associated measurement errors. In the preferred embodiment, the internal cavity of the end block is made to be six centimeters long between the two ends 73, 75 thereby separating the transducer from the cavity end wall by a distance which is greater than one and one half wavelengths of sound for the fluid with the highest sound velocity to be measured, in this case hydrogen gas, at the sound frequency to be used, in this case 40 KHz. This allows three full waves to be transmitted and received before reflection interference can occur. Other means to accomplish the same purpose could include filling the cavity of the end block with sound deadening material such as glass wool or creating the face of the end wall disposed opposite the diaphragm with a cone shaped or angled orientation which lessens the amount of sound reflected back to the diaphragm, or the transducers can be fitted directly onto the ends of the guide tubes 23, or any combination of these means.

It will be seen from the top plan view of FIG. 1B that the guide tube 23 is disposed offset to the sides of the transducers 25, 27. When using piezoelectric crystal transducers which operate in the 1:3 or "bending" mode, it has been found to be very important to mount the guide tube so that it transects the outer edge of the piezoelectric crystal beneath the metal diaphragm rather than in the center because it makes a large difference in the amplitude of the first few sound pulses. The sound transmitting and receiving transducers implemented in this way produce a rapid build-up of received oscillations. That is, the difference in amplitude, from amplitude peak to successive amplitude peak near the beginning of the sound pulse, is typically in excess of 200%. The "ring-up" of the narrow band width transducers such as are utilized in the preferred embodiment, having a "Q" in excess of 10, is typically on the order of about 10%. This implementation would seem contrary to intuitive analysis which would suggest that the tube should be disposed at the center of the transducers where the eventual amplitude of vibration of the diaphragm is the greatest.

It is not necessary to know the length of the guide tubes 23 or to make them an equal length between the transducer diaphragms 25, 27 because the test chambers are standardized using numerical factors which correct for differences in length and which are stored in the instrument controller's computer memory.

The guide tube 23 internal diameter is chosen to be one centimeter in order to accommodate typical fluid flow rates. The length of the guide tubes in the chambers of the preferred embodiment is chosen to be 30 centimeters so that the instrument can be packaged in a way which is convenient to locate in a semiconductor processing tool or near a process stream. Other sizes and lengths of guide tubes may be utilized in other embodiments, as long as the length to diameter ratio exceeds a factor of approximately 10. When it is less than 10, it has been found that sound waves which have been reflected from the walls of the guide tube will impinge on the receiving transducer soon enough after the onset of oscillation to distort that part of the received wave form to which the detector responds, causing measurement errors.

Sound induced into the guide tube 23 through the solid materials of construction is minimized for acoustic isolation by the following means: the several mechanical connections between the sound generating transducer 25 and the central block 31 are made with dissimilar materials thereby attenuating the amplitude of sound which is coupled by solid contact with each successive connection along the sound path. The guide tube 23 makes a mechanical connection only in the central block and is not connected to the sample return tubes 29 or to the end blocks 33. This assures that sound coupled to the guide tube by solid contact can only occur at the central block. Additionally, in its preferred form, the guide tube is made of a polymeric material such as fluorocarbon because such materials attenuate ultrasonic sound quickly. The use of the herein disclosed acoustic isolation techniques in combination with sound absorbing materials of construction assures that the amplitude of the sound conducted through the guide tube material and reaching the sound receiver is minimal compared to the amplitude of sound conducted through the fluid sample.

MULTIPLE GUIDE TUBE CHAMBERS

Reference is made to FIGS. 4 and 5 showing a train of sonic analyzers. The central block 33 design, which permits assembling several acoustic chambers together in an acoustic analyzer train, by placing the center blocks in contacting adjacent relation, also permits a serial fluid flow path through the several guide tube chambers of said train as follows: the first fluid flow is conducted through and exits the first chamber. This flow is then mixed with the second fluid flow and the resultant mixture is conducted through and exits the second chamber. This flow is then mixed with the third fluid flow and the resultant mixture is conducted through and exits the third chamber, and so on through all the chambers which comprise the instrument, which is usually as many chambers as there are individual fluids comprising the resultant mixture. The instrument repetitiously measures the time-of-flight of sound waves in the fluid contained in each of the chambers at approximately 100 Hz. All the chambers are maintained at the same temperature and pressure. A microprocessor is programmed to ratiometrically compare the time-based measurements of each fluid with those in the subsequent fluid mixture and to generate alarms and/or control signals for modulating valves if deviations beyond preselected limits are observed.

Reference is made to FIGS. 1A to 1C and 2 to 3C. An important aspect of the fluid introduction means is the incorporation of the recesses or machined seats 41 for compression fluid seals at opposite faces of the central block 31 at the fluid inlet and outlet channels whereby each central block mates with other central blocks comprising the analyzer train. As a result of the interconnecting of the inlet and outlet channels of the center blocks, the series of test chambers of an analyzer train are pneumatically interconnected so all measurements are made at the same pressure (however, the effect of pressure differences is negligible). When one or more of the fluids is delivered at a very low flow, a check valve 43 may be installed in the center block so as to prevent mixing in the direction counter to the fluid flow.

The stainless steel center blocks are disposed in an enclosure in physical abutting contact and share a common metal back plate (not shown) which acts as a heat distributor for temperature equalization whereby temperature differences between the gases in individual test chambers are minimized. As a result, the reference fluid is both pressure and temperature coupled to the sample fluids. All these important aspects described above are incorporated into each center block thereby permitting expansion of the number of chambers in an instrument simply by adding additional analyzer(s) to the analyzer train, which is, in itself, yet another important design feature.

When a septum or valve is installed between the chambers so as to isolate them, they can be connected for parallel flow. In this configuration the reference chamber may be either sealed or contain flowing fluid. The two chambers are maintained at the same temperature, as previously described.

Reference is made to FIG. 5 of the drawings for an illustration of a gettering section of the analyzer train. The apparatus is identical to the time-of-flight sonic analyzer except it lacks the electronics. The appropriate chemical system 81 for the desired gettering action is disposed in the sound wave guide tube 23. The fluid flow through the gettering section is the same as disclosed in FIG. 1F.

THE ELECTRICAL APPARATUS

The electrical apparatus of the present invention is unique to the method herein disclosed for comparison of near simultaneous sound velocities in the several chambers. Sound burst generators are provided for creating sound waves at one end of each chamber in response to electrical impulses. The sound burst generator assembly includes a transducer which is bonded to the isolation diaphragm. These transducer assemblies are a standard commercially available item of commerce (piezoelectric, available in the range of 20 KHz to 80 KHz). Other types of transducers which would work are electret, magnetic, and plastic piezoelectric. These transducers can also be used both as the transmitter and receiver. The response to the electronic impulses includes energizing the sound generating transducers which convert electrical impulses into mechanical motion and the mechanical motion is coupled to the fluid sample in each chamber by the isolation diaphragm.

The sound burst receiver assembly converts the sound waves it senses into electrical impulses. It is essentially the same as a sound burst generator except that an FET preamplifier is included.

THE ELECTRONIC APPARATUS

Reference is made to FIG. 6 of the drawings for an understanding of the electronic apparatus which is integrated with the mechanical and electrical apparatus.

A. THE INSTRUMENT CONTROLLER

The essential element of the electronic apparatus is the instrument controller. It is microprocessor-based and has the following functions:

1. It triggers the sound burst oscillator which creates a short burst of electrical alternating current signal at a set frequency upon receiving an electrical impulse from the instrument controller. This in turn actuates the sound burst generators in the various chambers.

2. It controls the multiplexers and interfaces with the signal processor, the latter including:
 (a) A multiplexer which allows the instrument controller to connect it to any one of the sound burst receivers;
 (b) A receiver disable which attenuates the sound burst receiver signal from the sound burst initiation until the voltage aberrations from cross-talk noise are below the voltage level resulting from the background noise. This eliminates the processing of any signal resulting from sound transmitted through the solid materials of construction of the guide tube or from spurious sources;
 (c) An input amplifier which amplifies the electrical energy from the sound burst receiver (whichever one is selected by the instrument controller and connected by the multiplexer) to the voltage level required for the proper operation of the signal processor;
 (d) A band pass filter which attenuates the elements of the electrical signal whose A-C frequencies are other than that created by the sound burst oscillator, thereby reducing vulnerability of the signal processor to the effects of background ambient noise and electrical noise;
 (e) A detector circuit which creates an electrical impulse corresponding to the precise moment the sound burst is received and serves to stop an electronic counter (timer) which was started at the onset of sound generation.
 (f) A timer—an electronic counter which is used to measure time-of-flight of sound waves.

3. The instrument controller interrogates and accepts data from the timer(s) contained in the signal processor(s). These data are the number of clock pulses accumulated between the moment a counter was started in response to the start of transmission of sound and the moment that counter was stopped in response to an electrical impulse received by the detector in the signal processor, as previously disclosed.

4. The instrument controller executes the calculations of the ratiometric comparative sensing method, in which it calculates the ratios of the sound velocity dependant measurements in successive pairs of the acoustic chambers or guide tubes. These calculations enable the following capabilities:
 (a) The "standardization" function whereby unequal distances between the sound sending and sound receiving transducers in the chambers are normalized. During the "standardization" step, the same fluid specie is introduced to all the chambers and sound velocity dependent measurements for each chamber are obtained. Ratios of successive pairs of these measurements are "normalization constants" and are stored in electronic memory and used in subsequent calculations to compensate for inequalities in sound path lengths. Standardization is disclosed in detail under "Method of Operation," section 4.

(b) The several "registration" functions wherein individual fluids, mixture compositions and fluid flows are "memorized" by the instrument controller: The "registration" functions are initiated by the user, during which the instrument controller obtains sound velocity dependent measurements in the fluids contained in its individual chambers, calculates ratios of said measurements in successive pairs of acoustic chambers to yield registration constants, and stores these in electronic memory as particular receipes. The instrument controller will retain several receipes and enter a specific one into its operating program upon user command. The various registration constants and their uses are disclosed in detail under "Method of Operation," section 5.

5. The instrument controller controls the man-machine interface.

(a) It accepts user-entered parameters such as set points for the portion of each individual fluid comprising the resulting mixture and deviation levels (from those set points) at which alarms should be actuated and stores these values in electronic memory.

(b) It compares the results of calculations made in (3) above to these data and actuates output devices such as meters and relays so as to communicate the results of these comparisons to the user.

6. The instrument controller enhances data quality with three software routines: Spurious Data Rejection, Digital Data Filtering, and Dynamic Data Correction. These are described as follows:

(a) Spurious Data Rejection: A data set is defined in the operating program as comprising a set number of individual time measurements. This number is sufficiently small to satisfy the Nyquist sampling criterion. When the data set is acquired, the instrument controller calculates its average value, then compares each individual measurement to said average value. Allowable deviations from the average value are set in the operating program. Those individual measurements which deviate from the average value for the data set by more than said allowable limits are eliminated from the data set. The instrument controller then calculates a new average value for the data set from the remaining individual measurements and utilizes said value for subsequent calculation steps.

(b) Digital Data Filtering: The instrument of the preferred embodiment is designed to function with low impedance fluids such as pure hydrogen gas (117 Rayls at one atmosphere pressure). It is nonetheless possible for data to be faulty due to low amplitude of received acoustic energy. The instrument controller is provided with the means to recognize this and to filter such faulty data out, this means herein called digital data filtering. When the received sound wave amplitude is too low for consistent detection of the arrival time of the first positive half wave, the individual time-of-flight measurements will correspond to the arrival times of either the first, second, third, etc. positive half waves. The standard deviation is computed for each data set and if said standard deviation exceeds a number stored in the operating program the data set is rejected. If said standard deviation is less than the stored number, the data set is accepted and stored in RAM and used for subsequent calculations.

(c) Dynamic Data Correction: Faulty data of another kind can result from more severe degradation of received sound wave amplitude and the detector consistently responding to the arrival time of the second, third, or even the fourth positive half wave in the sound pulse packet. The instrument controller has a means to recognize this and to correct such data, this means herein called dynamic data correction. Dynamic data correction includes an initialization routine, automatically executed whenever an instrument is put into operation or following power interruption. During initialization, data sets are acquired and passed through the spurious data rejection and digital data filtering routines earlier disclosed until ten are accepted. The microprocessor determines the average value of the ten and stores this value at three locations in RAM. The quantities stored in the three RAM locations are used to calculate a value herein designated "moving window average."

Each acquired data set's value is compared to the moving window average and if the data set's (average) value exceeds the moving window average by within pre-set limits the data set's value is automatically corrected by subtracting (or adding) from its value increments of time corresponding to the sound frequency period. In the preferred embodiment the sound frequency is 40 KHz, so the sound frequency period is 25 microseconds and the said pre-set limits of time are this frequency period plus and minus 5 microseconds which are allowed for fluid composition changes. The pre-set limits of time are therefore multiples of 25 microseconds plus and minus the allowed 5 microseconds. For example, assume that the most recent data set is accepted on the basis of its standard deviation and its average value exceeds the moving window average by 52 microseconds. THis falls within 45:55, so 50 microseconds are subtracted from the data set's average value.

As each data set exits the dynamic data correction routine its value is stored in the first RAM location, displacing the previous value to the second RAM location, the second to the third RAM location and the third is discarded. This results in the maintenance of a moving window average consisting of the values of the three most recent data sets.

The three software routines disclosed here need not be applied in the order disclosed, but may be applied in various orders so as to optimize an instrument's performance of different tasks. For example, Dynamic Data Correction may be applied to each measurement prior to Digital Data Filtering when fluid composition is subject to very rapid change.

7. The instrument controller interfaces to an external computer so as to allow it to establish set points, alarm deviation levels, and obtain data from the instrument controller for graphic presentation and data storage.

B. THE EXTERNAL COMPUTER

The software driving the external computer allows it to compute a receipe of fluid constituency and composition from known thermodynamic values of sound velocity at standard conditions and to enter the registration constants for fluid ratios and deviation alarms directly into the instrument controller's electronic memory. This is an alternative to registration with pure fluids and fluid mixtures actually flowing through the instrument's acoustic chambers and is accomplished by a means disclosed in detail hereinafter.

At this time registration constants for gas mixtures cannot be computed with great accuracy due to complex thermodynamic interactions. The value of an individual gas' heat capacity has been found to vary when it is mixed with different gas species. As a result, the accuracy of said calculations is seldom better than plus or minus 10 percent. As a practical alternative, the instrument of the preferred embodiment has been provided with a means to measure individual sound velocities of each mixture component. This means is disclosed in detail hereinafter. (Method of Operation, Section 8.) These measurements are then computed into setpoints and downloaded as disclosed hereinafter. Receipes computed from measured values have much higher accuracy than those computed from values obtained from calculation using only thermodynamic constants.

MEASUREMENT INTERLACING

The instrument of the present invention is designed to satisfy the Nyquist sampling criterion, where data is obtained at a frequency more than twice that of fluid composition change. At a flow rate of 10 liters per minute and with an internal volume of the acoustic analyzer of 0.125 liters, the fluid will be changed 80 times per minute, or 1.33 Hz. Data must therefore be obtained at greater than 2.67 Hz in order to satisfy the Nyquist criterion.

The digital data quality assurance routines disclosed previously herein require that a data set be defined as comprising a number of measurements, and sixteen is the number generally chosen. Because at least ten milliseconds must be allowed between successive measurements for acoustic echoes to attenuate in each acoustic analyzer, the instrument of the preferred embodiment is set to make measurements at 80 Hz in each acoustic analyzer. The 16 measurements comprising a data set can therefore be obtained in 200 milliseconds, or at a rate of 5 Hz, exceeding the Nyquist sampling criterion by approximately a factor of two.

Optimal simplicity, efficiency, and other advantages are obtained through the use of multiplexing where only one acoustic analyzer is electrically connected to the sound burst oscillator and the signal processor at any time. Acoustic isolation between the individual acoustic analyzers is less critical since only a single such analyzer is conducting sound at any time. Furthermore, since the same sound burst oscillator and signal processor are utilized for all measurements, any systematic measurement anomalies produced become cancelled in the ratiometric comparative sensing technique which is disclosed in detail later herein.

Multiplexing of both the sound burst oscillator and signal processor circuit, such that only a single acoustic analyzer is active at any moment and near simultaneous measurements are obtained allows time for residual sound to die down between successive measurements in each analyzer. Up to 8 acoustic analyzers may be so multiplexed in a single instrument with no degradation in measurement quality with respect to the Nyquist sampling criterion. Said multiplexing is herein referred to as "measurement interlacing."

TRUE TIME-OF-FLIGHT DETECTION

The measurement technique employed in the preferred embodiment is based on ratiometric comparison of times-of-flight and requires that the value of the exact arrival time of the acoustic signals be utilized in the calculations. The detection means to accomplish this are disclosed as follows, and reference is made to FIG. 8 of the drawings which is a circuit logic diagram for the clock enable circuity:

The acoustic oscillator polarity and the polarity of the crystals in the transducers are oriented such that a negative half wave is produced at the onset of received sound energy. A voltage comparator's threshold is set by a potentiometer to a value significantly above the electrical and ambient acoustic noise level so as to generate an output at logic state "0" whenever no transmitted sound energy is detected, and an output at logic state "1" in response to the positive portion of the electronic signal resulting from reception of the chamber's acoustic signal. (Opposite polarities may be utilized.)

Reference is made to FIG. 7 which is a time diagram for the detector logic circuitry. Thereshown are the signal waveforms which would appear on an oscilloscope when the time dependent measurements are made in an analyzer of the present invention:

FIG. 7A is the waveform of the signal (arbitrarily selected 2 separate 40 Kilohertz energizing pulses) which actuates the sound burst generator;

FIG. 7B is the waveform of the signal generated by the sound burst receiver (2 humps are cross-talk or remanent noise). Waveforms are squared off to show wave low amplitude details at beginning of reception of sound wave;

FIG. 7C is the waveform of the signal used to prevent false detector actuation by the cross-talk or remanent noise;

FIG. 7D is the waveform of the signal of the output of the voltage threshold detector after receiver blanking has been effected;

FIG. 7E is the waveform of the signal which sets the timing counters to zero when the signal goes to logic state zero;

FIG. 7F is the waveform of the signal that enables the timing counters when in logic state zero (in the timing duration, interval $t_1$ is the time period during which the timer accumulates pulses at one-half the master oscillator frequency and $t_2$ is the time period when the timer accumulates pulses at the master oscillator frequency);

FIG. 7G is the waveform of the signal of the master oscillator;

TRANSMX (FIG. 7A): Receives a logic "1" signal from the sound burst oscillator whenever said oscillator is active, i.e., sound is transmitted; and a logic "0" signal at all other times; and COMP OUT (FIG. 7D): Receives the logic signal from the voltage comparator whose function is described above.

Reference is made again to FIG. 8.

OPERATION OF STAGE 1: an inverter U1A inverts the comparator signal so that it is logic state "1" when no acoustic signal is received, and so that it is in state "0" whenever the positive portion of the received waveform exceeds the comparator's voltage trigger threshold. A second inverter U2A inverts the transmit signal so as to produce a logic state "0" when the sound burst oscillator is activated. This signal then serves to reset a flip-flop logic gate U3A into a logic state "0" when the sound burst oscillator is activated. This flip-flop logic gate U3A is set into the logic state "1" when the first sound pulse is detected. Since the flip-flop is positive edge triggered and the comparator signal is inverted, the actual transition of the flip-flop output occurs at the falling edge of the comparator signal. The flip-flop output therefore is a transition from logic "1" to "0" upon beginning of sound sending and "0" to "1" as the voltage corresponding to the received acoustic signal falls below the detector voltage threshold;

OPERATION OF STAGE 2: stage 2 is analogous to stage 1 except that inverter U1A is eliminated. The output of the flip-flop U1B transitions from logic state "1" to "0" at the beginning of sound sending and from logic state "0" to "1" as the voltage corresponding to the received acoustic signal rises above the detector voltage threshold; and OPERATION OF STAGE 3: a master oscillator signal is inverted by an inverter U1C and the inverted signal is the clock (CLK) input to the D-flip-flop U2C. Said flip-flop is configured such that it will transition at each rising edge of the CLK input. The output of the flip-flop is a square wave at half the frequency of the CLK input. The outputs of stages 1 and 2 (ENBA and ENBB) are the inputs to an "exclusive or" gate U2C causing its output to be logic state "0" except during the interval when the voltage level of the received acoustic signal exceeds the threshold of the detector when it will be logic state "1 . " "And" gate U3C is connected to the output of the flip-flop and the output of U5C. Its output will then be logic state "0" except during the above-described interval when it will be a square wave of half the master oscillator frequency. The inputs of "or" gate U4C are ENBA (from Stage 1) and the output of U3C. The output of U4C transitions from logic "1" to logic "0" at the beginning of sound transmission and will flip-flop at half the oscillator frequency during the interval when the voltage level of the received acoustic signal exceeds the threshold of the detector and will then transition to the logic state "1" until reset.

The output of stage 3 (U4C) serves as the enable for the counter circuitry, which accumulates clock pulses at the frequency of the master oscillator between the beginning of sound transmission and the instant the received sound signal level exceeds the detector voltage threshold, and then accumulates clock pulses at half the frequency of the master oscillator between that instant and the instant the received sound signal drops below the detector voltage threshold. The result is a number of counts corresponding to the arrival of the peak amplitude (FIG. 7B-b) of the first positive half wave of the acoustic signal. The instrument controller acquires the count data and calculates the arrival time of the leading edge of the pulse packet (FIG. 7B-a) by taking into account the 270 degrees of phase existing between said count data and the actual moment of arrival of acoustic energy and backcounting to the actual moment of arrival by subtracting the count corresponding to the 270 degrees of phase from said count data. The master oscillator's frequency is divided by a numerical constant to produce the frequency of the acoustic wave oscillator. The count corresponding to 270 degrees of phase is therefore a numerical constant in the instrument controller's memory enabling it to subtract precisely 270 degrees of phase regardless of drift in either oscillator.

The detection principle herein disclosed contemplates the measurement of successive half waves in the same pulse packet in order to improve measurement precision.

The time-of-flight detection principle and its implementations herein disclosed represent improvements in time-of-flight measurement technology because they eliminate the need for separate arming and triggering steps, threshold voltage adjustment, and control of the level of the received sound signal such as are required in the Smalling U.S. Pat. No. 4,596,133. When this detection principle is combined with the ratiometric comparative sensing technique, an instrument is embodied in which all sources of measurement error are symmetrical, measurement accuracy is absolute, and measurement precision is limited only by signal energy level, signal aberrations, and precision of the electronic components.

This detection principle further provides a means to check the sound generating and receiving apparatus and the signal processors for proper operation. If a logic state "1" is not attained following actuation of the sound generating transducer assembly, the counter will overflow and the instrument controller will recognize that a malfunction has occurred.

METHOD OF OPERATION

This is a description of the ratiometric comparative sensing technique as it is used in the instrument of the preferred embodiment of the present invention:

1. Time-of-flight measurements are related to sound velocity by the equation:

$$VT = L \qquad 1.$$

where V represents velocity, T the time-of-flight, and L the length of the acoustic path.

2. The effects of temperature: Sound velocity in gases is expressed as:

$$V = \sqrt{\frac{RT\delta}{M}} \qquad 2.$$

where $\delta$ is the ratio of the specific heats $$\frac{CP}{CV},$$

R is the universal, gas constant, T is the absolute temperature, and M is the molecular weight.

In the prior art embodiments, changes in sound velocity are measured.

$$V_1 - V_2 = \sqrt{\frac{RT\delta_1}{M_1}} - \sqrt{\frac{RT\delta_2}{M_2}} = \sqrt{RT}\left(\sqrt{\frac{\delta_1}{M_1}} - \sqrt{\frac{\delta_2}{M_2}}\right) \qquad 3.$$

Equation 3 shows that the value of temperature is a multiplier and therefore must be measured or known.

The comparative method disclosed herein is based on ratios of sound velocities:

$$\frac{V_1}{V_2} = \frac{\sqrt{\frac{RT\delta_1}{M_1}}}{\sqrt{\frac{RT\delta_2}{M_2}}} = \sqrt{\frac{\delta_1 M_2}{\delta_2 M_1}} \qquad 4.$$

Temperature cancels out of the equation, and thus need not be measured or known so long as all measurements are made at the same temperature. The instrument design provides for this.

Higher order temperature effects: At temperatures normally encountered, which are near ambient, the values of $\delta$ vary less than one part per thousand per degree centigrade. Therefore, when all measurements are made at the same temperature and the ratiometric comparative sensing technique is employed, no separate temperature measurement or corrections are necessary.

3. Linearity of the ratiometric comparison method: chambers;

The subscripts utilized below are defined as follows:
(a) Subscripts 1, 2, 3, etc. denote sequential
(b) Subscripts A, B, C, etc. denote times-of-flight of the individual fluid species;
(c) Subscripts m1, m2, m3, etc. denote times-of-flight of fluid mixtures in individual acoustic analyzers; and
(d) X represents mole fraction.

From the mixing rule:

$$X_A + X_B + X_C + etc. = 1 \qquad 5.$$

Fluids are added and mixed serially, as previously described. With the exception of chamber #1, each chamber contains a binary mixture composed of two fluids and under stable flow conditions each is of stable composition. Using the mixing rule for a binary mixture:

$$X_A + X_B = 1 \qquad 6.$$

and:

$$X_A = 1 - X_B \qquad 7.$$

The time-of-flight of sound waves in a fluid mixture are expressed as:

$$T_{m1} T_A X_A + T_B X_B \qquad 8.$$

Substituting equation 7:

$$T_{m1} = T_A(1 - X_B) + T_B X_B \qquad 9.$$

Expressing the ratio:

$$\frac{T_{m1}}{T_A} = \frac{T_A(1 - X_B)}{T_A} + \frac{T_B X_B}{T_A} \qquad 10.$$

Rearranging the equation:

$$\frac{T_{m1}}{T_A} = \left(\frac{T_B}{T_A} - 1\right) X_B + 1 \qquad 11.$$

Note: The left side of equation 11 contains the ratio $T_{M1}/T_A$ which represents the ratio of two times-of-flight of sound waves at the temperature of the instrument. The right side of equation 11 contains the ratio $T_B/T_A$ which represents the ratio of two times-of-flight at standard temperature (25 degrees Celcius). The two $T_A$s are obviously different and it would appear at first glance that the equality is violated. However, since equation 3 states that the ratio of two times-of-flight (or resonant frequencies) is constant at all temperatures, the left side of equation 11 is equal to the ratio of the two times-of-flight which would be measured at standard temperature; That is: $T_{M1}/T_A$ at any temperature equals $T_{M1}/T_A$ at 25 degrees Celcius. Therefore, equation 11 is valid.

A linear equation of the form $Y = MX + B$ is obtained where: $T_{M1}/T_A$ is the measured time-of-flight ratio corresponding to Y.

$$\left(\frac{T_B}{T_A} - 1\right)$$

are constants and correspond to M.

1 is a constant corresponding to B.

$X_B$ is the variable to be determined and corresponds to X.

The ratio $T_{M1}/T_A$ is seen to be a linear function of mole fraction $X_B$, since all other terms are constants.

4. Normalizing of the distances between transducers in each acoustic analyzer with the ratiometric comparative sensing technique: since individual lengths of the various acoustic analyzers comprising an instrument vary, the ratiometric comparative sensing technique herein disclosed provides a means for the normalization of the individual lengths of the multiple chambers. A "normalization" function is provided for this. Rearranging Equation 1:

$$V = L/T \qquad 12.$$

where V denotes velocity, L the length of the acoustic analyzer, and T the time-of-flight.

The same gas specie is introduced simultaneously into all the acoustic analyzers and the individual times-of-flight are measured. From the above equation:

$$V = \frac{L_1}{T_1} = \frac{L_2}{T_2} = \frac{L_3}{T_3}, etc. \qquad 13.$$

and:

$$\frac{L_1}{L_2} = \frac{T_1}{T_2}, \frac{L_2}{L_3} = \frac{T_2}{T_3}, etc. \qquad 14.$$

The Ls of the different chambers are related to each other as follows:

$$\frac{T_1}{T_2} = K_{n1}, \frac{T_2}{T_3} = K_{n2}, etc. \qquad 15.$$

where $K_{n1}$, $K_{n2}$, etc., are the normalization constants. Therefore:

$$\frac{T_1}{T_2 K_{n1}} = \frac{T_2}{T_3 K_{n2}} = \frac{T_3}{T_4 K_{n3}}, etc. = 1 \qquad 16.$$

5. Registration of a fluid composition receipe using the ratiometric comparative sensing technique: when the components of a fluid mixture are properly adjusted and serially flowed through the instrument, the instrument can "memorize" said mixture by calculating registration constants and storing those constants in electronic memory. Before registration of a fluid mixture the times-of-flight are: $T_1$, $T_2$, $T_3$, etc.

Upon registration, ratios are calculated as follows:

$$\frac{T_1}{T_2 K_{n1}} = K_{R1}, \frac{T_2}{T_3 K_{n2}} = K_{R2}, \text{etc.} \qquad 17.$$

and $$\frac{T_1}{T_2 K_{n1} K_{R1}} = \frac{T_2}{T_3 K_{n2} K_{R2}}, \text{etc.} = 1 \qquad 18.$$

where $K_{R1}$, $K_{R2}$, etc. are registration constants.

6. Measurement and registration of flow velocity: Two acoustic analyzers are used, with one arranged for normal sample introduction and the second arranged for flow measurement (FIG. 3). No fluid is added to the second acoustic analyzer so both contain the same flowing sample.

Rearranging equation 1:

$$T = L/V \qquad 19.$$

Combining equations 14 and 15:

$$\frac{L_1}{L_2} = \frac{T_1}{T_2} = K_{n1} \qquad 20.$$

Solving for $L_1$:

$$L_1 = K_{n1} L_2 \qquad 21.$$

Combining equations 19, 20 and 21:

$$\frac{T_1}{T_2} = \frac{L_1 V_2}{L_2 V_1} = \frac{K_{n1} L_2 V_2}{L_2 V_1} = K_{n1} \frac{V_2}{V_1} \qquad 22.$$

Since the same fluid composition is flowing in both acoustic analyzers, but in the first sound waves are traversing equal distances of opposite directions of flow and in the second all the fluid flow is in the direction (or opposite the direction) of sound wave propagation, any apparent deviation from unity of sound velocity ratio is a measure of the ratio of fluid flow to sound velocity in that fluid:

$$\frac{T_1}{T_2 K_{n1}} = \frac{V_1 + V_F}{V_1} = K_{F1} \qquad 23.$$

where $V_F$ is flow velocity, and:

$$\frac{T_1}{T_2 K_{n1} K_{F1}} = \frac{T_2}{T_3 K_{n2} K_{F2}}, \text{etc.} = 1 \qquad 24.$$

where $K_{F1}$, $K_{F2}$, etc. are flow registration constants.

Equation #11 demonstrates that the time-of-flight ratios calculated in the ratiometric comparative sensing technique are linear functions of deviations from flow setpoints.

7. Registration of individual fluid constituents prior to mixing. The ratiometric comparative sensing technique may be used in such a way as to enable the instrument of the preferred embodiment to confirm that the correct individual fluids are utilized for mixing. Check valves are installed between the individual acoustic analyzers to allow only forward serial flow. Fluid A fills analyzer #1, then the flow of fluid A is stopped. Fluid B fills analyzer #2, then the flow of fluid B is stopped. The check valve prevents fluid B from entering analyzer #1 and mixing with fluid A contained therein. This process is iterated for all the acoustic analyzers comprising the instrument. Alternatively, a parallel flow configuration may be utilized. The individual times-of-flight are measured by the instrument and are here represented as $T_1$, $T_2$, $T_3$, etc.

The unit has previously been normalized, so, when the individual fluids are contained in individual analyzers, $$\frac{T_1}{T_2 K_{n1}} = K_{C1}, \frac{T_2}{T_3 K_{n2}} = K_{C2}, \text{etc.} \qquad 25.$$

$$\frac{T_1}{T_2 K_{n2} K_{C2}} = \frac{T_2}{T_3 K_{n2} K_{C2}} = \frac{T_3}{T_4 K_{n3} K_{C3}}, \text{etc.} = 1 \qquad 26.$$

where $K_{C1}$, $K_{C2}$, etc. are the fluid component constants.

8. Obtaining sound velocity dependent measurements in an unknown fluid: Two acoustic analyzers are utilized: analyzer #1 herein designated reference and analyzer #2 designated sample. A fluid of known sound velocity, for example, dry air, hydrogen, nitrogen, etc., fills the reference acoustic analyzer and the unknown fluid fills the sample acoustic analyzer. The flow path is set for parallel flow so that no fluid mixing occurs. Sound times-of-flight are measured.

Rearranging equation 1.

$$T = L/V \qquad 19.$$

Combining equations 14 and 15:

$$\frac{L_1}{L_2} = \frac{T_1}{T_2} = K_{n1} \qquad 20.$$

Solving for $L_1$:

$$L_1 = K_{n1} L_2 \qquad 21.$$

Combining equations 19, 20 and 21:

$$\frac{T_1}{T_2} = \frac{L_1 V_2}{L_2 V_1} = \frac{K_{n1} L_2 V_2}{L_2 V_1} = K_{n1} \frac{V_2}{V_1} \qquad 22.$$

Rearranging equation 22:

$$\frac{T_1}{T_2 K_{n1}} = \frac{V_2}{V_1} \qquad 27.$$

The sound velocity for the unknown fluid at standard conditions is calculated directly (at any temperature) from the measured time-of-flight data using a fluid of known sound velocity and the ratiometric comparative sensing technique since $T_1$ and $T_2$ are measured, $V_1$ is known, and $K_{n1}$ is a constant.

9. Computation and loading a fluid composition receipe using an external computer: actual velocities for the mixture components must be known and entered into the computer program. (The instrument includes a means to measure these which was disclosed previously.) The desired mole fractions for each component of the mixture to be created are then entered. Next, the order of component mixing is entered. The computer program calculates the mole fraction (X) for each stage of the mixing process using equation 6 and calculates the registration constants $K_{R1}$, $K_{R2}$, etc. using equation 17 for each mixing step. The computed registration constants are transferred to the instrument controller which stores them in electronic memory. Maximum allowable deviation limits are calculated in the same manner and stored in the instrument controller's electronic memory.

ADVANTAGES AND IMPROVEMENTS

Some prior art such as the Panametrics U.S. Pat. No. 4,596,133 utilizes acoustic time-of-flight measurements in such a way as to enable measurements in a process stream where fluid flow rates can change rapidly. The technique utilized is one in which sound waves are sent alternately in the direction of, and opposite to, the direction of process fluid flow. This technique allows the calculation of both sound velocity and flow velocity from time-of-flight measurements. Average molecular weight of the fluid mixture is estimated by use of relationships between heat capacity, molecular weight and temperature to sound velocity. Temperature must be measured, either by a temperature sensor or by use of a temperature dependent characteristic of the transducer assemblies, and the analytical results corrected for temperature. This prior art utilizes, in effect, a single chamber, the process conduit comprising that chamber, and no guide tube for the purpose of conducting sound waves.

Other prior art such as described in the November 1986 *Review of Scientific Instruments* article utilizes a single resonating chamber to obtain sound velocity based measurements.

Still other prior art (the *Nuclear Instruments and Methods in Physics Research* article) presents an evaluation of different methods for calculating sound velocity in binary gas mixtures and reports the correlation between calculations utilizing different equations of state and actual tests. The research reported in this article is directed entirely toward the evaluation of different equations for sound velocity calculation. The apparatus utilized is a single time-of-flight chamber of the style utilized for such measurements for half a century. Sound velocities are compared by difference following temperature measurement and data correction.

The authors report that sound velocity calculations for gas mixtures are inherently inaccurate and that in order to accurately estimate binary gas compositions from sound velocity based data it is necessary to make many time-of-flight measurements at varying mole fractions for each binary mixture, create a "look-up" table, and interpolate between the individual values. A computer may be used for this purpose. The present invention circumvents these problems by its allowing for empirical registration of setpoints, as previously described, and reporting deviations from those setpoints.

In all of the prior art, the measurement technique compares sound velocity based quantities by difference but not by ratio, and temperature measurement is necessary.

The instrument and method of the present invention embodies improvements in all aspects of the prior art. By relating the frequencies of the acoustic oscillator (used for sound pulse generation) and the master oscillator (used for time-of-flight clocking), true time-of-flight measurements are made possible. These measurements are independent of instrument operating parameters such as signal amplitude and detector voltage threshold. The ratiometric comparative sensing technique permits the instrument to produce data which do not have a drift component. In fact, the instrument of the present invention has no systematic error and since sound velocity in a fluid is a physical attribute, setpoint receipes can be transferred between separate instruments. Fluid composition analysis with this instrument and method needs no re-calibration.

The present invention and method for nearly simultaneous measurements using multiplexing and interlacing in multiple chambers with flowing samples and either sequential, parallel, or serial flow paths permit simple sound velocity dependent time-based measurements of binary mixtures to be combined to yield constituent analysis of the individual fluid mixture components.

The method of ratiometric comparison of measurements which are dependent on sound velocity simplifies computations and facilitates automation for practical industrial use. The need to measure and correct for temperature variations is eliminated. Normalization of individual guide tube lengths following disassembly and maintenance is simplified, as are registrations of mixture compositions, flows, and fluid components. The provision for empirical establishing of setpoints is a practical innovation which permits existing fluid blending operations to benefit from acoustic fluid composition monitoring. Setpoints may also be established with a computer program and stored in the instrument. The computer program requires that sound velocities of individual fluid mixture components be known, and measurement of sound velocities in unknown fluids is provided for in the instrument and method by reference to a known fluid. All deviations from composition and flow setpoints are linear. None of these practical advantages have been suggested by the prior art.

CONCLUSION

It will be apparent from the foregoing description of the invention, in its preferred form, that it will fulfill all the objects and advantages attributable thereto. While it is illustrated and described in considerable detail, the invention is not to be limited to such details as have been set forth except as may be necessitated by the appended claims.

We claim:

1. A fluid analysis instrument comprising,
   at least one acoustic analyzer having means for introducing fluid samples there into,
   means for maintaining all samples at the same temperature during analysis,
   means for creating and detecting sound in said analyzer,
   means for making time based electronic measurements from which either the resonant frequency or time-of-flight of sound in the analyzer can be determined, and
   means for ratiometrically comparing said time-based measurements of the same type to verify correct fluid constituents, and to determine fluid composition.

2. The fluid analyzer of claim 1 wherein the means for creating and detecting sound in said analyzer and the means for determining the time-based measurements in the analyzer include
   a continuous wave sound generator for creating a continuous acoustic wave in said acoustic analyzer,
   means for varying the frequency of said acoustic wave to obtain maximum resonance,
   means for measuring the resonant frequency of the continuous wave in the acoustic analyzer thereby deriving the frequency period of sound in the fluid samples in the analyzer, and means for ratiometrically comparing the sound frequency periods for different fluid samples.

3. The fluid analyzer of claim 1 where in the means for creating and detecting sound in said analyzer and the means for determining the time-based measurements in the analyzer include means for generating a sound burst at an end of said acoustic analyzer in response to an electrical impulse, means for receiving a sound burst disposed at an end of said acoustic analyzer and for converting a sound burst which has traversed the fluid(s) contained in said analyzer into electrical impulses, means for measuring the time lapse between the initiating electrical impulse of a sound burst and reception of the electronic impulses from the sound burst receiver, and means for ratiometrically comparing time lapses for different fluid samples on the basis of the ratios of times-of-flight of the sound burst through the fluid in the analyzer.

4. The fluid analyzer of claim 1, 2 or 3 including means for utilizing the ratiometric comparison whereby deviations from unity activate alarms to alert observers or actuate fluid flow control mechanisms.

5. The fluid analyzer of claim 1, 2 or 3 wherein a multiplicity of acoustic analyzers are utilized and the flow of fluids in a sample stream is serial through the multiplicity of acoustic analyzers, and the addition of fluid flow components to the sample stream is also serial with one additional fluid being added to the sample stream per acoustic analyzer.

6. The fluid analyzer of claim 1, 2 or 3 wherein a multiplicity of acoustic analyzers are utilized and the flow of fluids in the acoustic analyzers are parallel and there is no mixing of the fluid samples.

7. The fluid analyzer of claim 1, 2 or 3 wherein a multiplicity of acoustic analyzers are utilized and the flow of fluids in a sample stream is serial through fewer than all of the analyzers and the addition of fluid flow components to the sample stream is also serial with one additional fluid being added to the sample stream per acoustic analyzer, and the flow of fluids is parallel in fewer than all of the analyzers and in other than those through which the flow is serial and there is no mixing of those fluids where the flow is parallel.

8. An analytical apparatus for monitoring and controlling fluid constituency, composition, and flow by measurements which depend on sound velocity comprising at least one acoustic analyzer having a fluid sample containment chamber with a sound wave guide tube disposed therein, means for introducing fluid sample flow into the center of said chamber and conducting it in opposite directions to the ends of the chamber through said guide tube, means for ingesting the fluid flow from the ends of the guide tube and discharging the fluid flow from the chamber, means for maintaining all fluid samples at the same temperature during analysis, a sound burst generator including a transducer disposed at one end of said chamber formed for generating a sound burst in said sound wave guide tube in response to an electrical impulse, a sound burst receiver including a transducer disposed at the other end of said chamber, said receiver formed for converting a sound burst which has traversed the length of said guide tube into electrical impulses, means for measuring the time lapse between the electrical impulse which initiates the sound burst and the respective electronic impulses generated by the sound burst receiver, and means for ratiometrically comparing time lapses for different fluid samples on the basis of the ratios of times-of-flight of the sound burst through the fluid in the analyzer.

9. The apparatus of claim 8 wherein the length over diameter ratio for the guide tube internal bore is greater than 10.

10. The apparatus of claim 8 wherein the guide tube disposed in said chamber is made of a chemically inert generally mechanically rigid material having a complex molecular structure for converting sound energy in the material into heat so that sound energy in the material is strongly attenuated and so that the guide tube itself does not function as an acoustic conductor.

11. The apparatus of claim 10 wherein the material of said guide tube is a polymeric.

12. The apparatus of claim 8 wherein the sound burst generator and receiver disposed in said analyzer include transducers disposed outside of the sample containment chamber.

13. The apparatus of claim 12 wherein the transducers are bonded to corrosion resistant diaphragms which isolate the transducers from the fluids being tested.

14. The apparatus of claim 8 wherein said chambers are provided with manifolding disposed mid-length thereof for releasing the sample fluids in the center of the guide tube and for ingesting the return flow of sample fluid from the ends of the chamber and expelling the sample gas to a process stream or into another acoustic analyzer chamber.

15. The apparatus of claim 14 wherein the manifolding is formed in a high heat transfer corrosion resistant material center block which can be mated in pressure and temperature coupled successive relation to form a train of analyzers.

16. The apparatus of claim 14 wherein said manifolding contains check valves to prevent back flow of fluids.

17. The apparatus of claim 8 wherein acoustic isolation is achieved by mounting the sound burst generator and receiver in blocks disposed at the opposite ends of the chamber, said blocks being made of a chemically inert generally mechanically rigid material having a complex molecular structure for converting sound energy in the material into heat so that sound energy in the material is strongly attenuated.

18. The apparatus of claim 8 wherein a multiplicity of acoustic analyzers are utilized and the flow of fluids in the sample stream is serial through the multiplicity of analyzers and the addition of fluid flow components is also serial with one additional fluid being added to the sample stream per acoustic analyzer.

19. The apparatus of claim 8 wherein a multiplicity of acoustic analyzers are utilized and the flow of fluids in the acoustic analyzers are parallel and there is no mixing of the fluid samples.

20. The apparatus of claim 8 wherein a multiplicity of acoustic analyzers are utilized and the flow of fluids in a sample stream is serial through fewer than all of the analyzers and the addition of fluid flow components to the sample stream is also serial with one additional fluid being added to the sample stream per acoustic analyzer, and the flow of fluids is parallel in fewer than all of the analyzers and in other than those through which the flow is serial and there is no mixing of those fluids where the flow is parallel.

21. An analytical apparatus for monitoring and controlling fluid constituency, composition, and flow by measurements which depend on sound velocity comprising at least one acoustic analyzer having a fluid sample corrosion-resistant containment chamber with a sound wave guide tube disposed therein, said guide tube having an L/D ratio for its internal bore greater than 10 and being made of a polymeric material, a center block manifold formed of a high heat transfer corrosion-resistant material disposed mid-length of the chamber and formed to introduce fluid sample flow into the center of said guide tube and conducting said flow in opposite directions to the ends of the chamber through said guide tube and ingesting the return fluid flow from the ends of the chamber for expelling the fluid flow from the chamber to a process stream or into another acoustic analyzer chamber, said center block being mateable in pressure and temperature coupled successive relation to other center blocks to form a train of analyzers, a pair of polymeric end blocks secured to and sealing the ends of the containment chamber, a sound burst generator including a transducer mounted in one of said end blocks disposed at one end of said chamber formed for generating a sound burst in said sound wave guide tube in response to an electrical impulse, a sound burst receiver including a transducer mounted in the other of said end blocks, said sound burst receiver formed for converting a sound burst which has traversed the length of said guide tube into electrical impulses, said transducers being bonded to corrosion-resistant diaphragms which isolate the transducers from the fluids being tested, means for measuring the time lapse between the electrical impulse which initiates the sound burst and the electronic impulse generated by the sound burst receiver, and means for ratiometrically comparing time lapses for different fluid samples on the basis of the ratios of times-of-flight of the sound burst through the fluid in the analyzer.

22. The apparatus of claim 21 wherein said guide tube is disposed to transect the edges rather than the middle of the transducer which is bonded to the isolation diaphragms.

23. The apparatus of claim 21 including means for utilizing the ratiometric comparison whereby deviations from unity actuate alarms to alert observers or actuate fluid flow control mechanisms.

24. A method for monitoring the constituency, composition, and flow of a gas mixture comprising the steps of introducing a sample gas mixture being monitored into an acoustic analyzer, creating sound in the sample, determining the time-of-flight of a sound wave in the sample or the frequency period for a sound wave in the analyzer, storing the time-based measurement in memory for comparison with subsequent time-based measurements of the same kind, routing the sample gas mixture through a suitable chemical getter to selectively and completely remove a specific gas constituent therefrom, reintroducing said altered sample being monitored into the analyzer at the same temperature, creating sound in the altered sample, determining the same time-based measurement of the sound in the altered sample as in the original sample, ratioing the time-based measurement of the original sample to the altered sample, repeating the foregoing steps, comparing the ratios to set points, and activating alarms or actuating flow control mechanisms if the ratios vary beyond a preselected variance limitation.

25. A method for monitoring the constituency, composition, and flow of a fluid mixture comprising the steps of introducing a sample gas mixture being monitored into an acoustic analyzer, creating sound in the sample, determining the time-of-flight of a sound wave in the sample or the frequency period for a sound wave in the analyzer, storing the time-based measurement in memory for comparison with subsequent time-based measurements of the same kind, introducing a second fluid sample being monitored into the analyzer at the same temperature as the first sample, creating sound in the second sample, determining the same time-based measurement of the sound in the second sample as in the first sample, ratioing the time-based measurement of the first sample to the second, repeating the foregoing steps, comparing the ratios to set points, and activating alarms or actuating flow control mechanisms if the ratios vary beyond a preselected variance limitation.

26. The method of claim 25 wherein a multiplicity of analyzers are temperature coupled to each other for nearly simultaneous time-based measurements of different samples in separate analyzers.

27. The method of claim 26 wherein the flow of fluids through the multiplicity of analyzers is serial and the addition of fluid flow components to the sample stream is also serial with one additional fluid being added to the sample stream per analyzer.

28. The method of claim 26 wherein the flow of fluids through the multiplicity of analyzers is parallel and there is no mixing of the fluid samples.

29. The method of claim 26 wherein the flow of fluids in a sample stream is serial through fewer than all of the analyzers and the addition of fluid flow components to the sample stream is also serial with one additional fluid being added to the sample stream per acoustic analyzer, and the flow of fluids is parallel in fewer than all of the analyzers and in other than those through which the flow is serial and there is no mixing of those fluids where the flow is parallel.

30. The method of claim 26 wherein the comparison of the time-based measurements for the sample with reference mixture is done automatically by computer, both mixtures being sonically pulsed periodically with a sound burst to detect any changes in the time-based measurements between the two.

31. A method for monitoring the constituency, composition, and flow of a fluid mixture comprising the steps of
    introducing a sample fluid mixture being monitored into an acoustic analyzer,
    providing a reference fluid mixture in a second acoustic analyzer at the same temperature as the sample mixture,
    converting electrical impulses into sound bursts which are sent through the fluid mixtures in the analyzers,
    sensing the sound bursts and converting the sensed sound bursts into electrical impulses,
    measuring the time lapse between the electrical impulses which initiate the sound bursts in each mixture and the on-set of the resulting electrical impulses generated by the sound burst sensing means,
    ratiometrically comparing the time lapse for the sample mixture with the time lapse for the reference mixture, and
    activating alarms or actuating flow control mechanisms when the ratios vary beyond a preselected variance limitation for the sample mixture being monitored.

32. In an analytical apparatus based on comparisons of numbers obtained from the velocity of sound in fluid mixtures, the method for determining true time-of-flight comprising
    deriving the location in time of a point of known phase from the onset of sinusoidal oscillation by electronically measuring the arrival time of two points on said sinusoidal oscillation, the location of said points being locally symmetric with the point of known phase to be derived, and
    subtracting the time interval corresponding to the known phase of the frequency period of said sinusoidal oscillation, said result being the on-set of reception of the sinusoidal oscillation, the true time-of-flight being the time lapse between the on-set of transmission and the on-set of reception of the sinusoidal oscillation.

33. In an analytical apparatus based on comparisons of numbers derived from the velocity of sound in fluid mixtures, the method for ratiometric comparative sensing for eliminating the need to know or control the temperature of the fluid mixtures being measured, the steps comprising
    making all measurements in the apparatus at the same temperature, and
    ratiometrically comparing measurements derived from the velocity of sound in fluids such that the temperature factor is identical and appears in both the numerator and denominator of said ratios and reduces to unity and therefore has no effect on the values of said ratios.

34. In an analytical apparatus employing a multiple of acoustic analyzers for obtaining measurements derived from the velocity of sound in fluids, a comparative sensing technique where numerical factors are obtained which eliminate the need to know the length of the individual acoustic analyzers or the need to provide acoustic analyzers of the same length, the steps comprising
    introducing a fluid sample of the same species of fluid into all acoustic analyzers at the same temperature,
    obtaining sound velocity-derived measurements for each acoustic analyzer containing said samples,
    ratiometrically comparing pairs of measurements for the different acoustic analyzers to obtain numerical factors,
    storing said numerical factors for use with measurements from unknown fluid samples, and
    upon obtaining measurements derived from sound velocity of unknown fluid samples, utilizing said numerical factors to eliminate the effects of analyzer length.

35. The method of claim 34 wherein additional numerical factors can be obtained for the purpose of establishing setpoints for subsequent monitoring of deviations from those setpoints when constituent fluid species or resulting fluid mixtures are introduced into the individual acoustic analyzers, said method eliminating the need to know the velocity of sound in any of the fluid species in which the sound-based measurements are obtained.

36. The method for operating a multiple of acoustic analyzers for obtaining nearly simultaneous measurements derived from the velocity of sound in various fluid mixtures comprising
    electronically connecting a sound burst oscillator to a single sound burst generator,
    electronically connecting a signal processor to the sound burst receiver contained in the same acoustic analyzer as the sound burst generator, and
    sequentially commutating the connections to the sound burst generators and the sound burst receivers of each of the acoustic analyzers to effectively make measurements on one analyzer of the series at a time in a sequence which leaves sufficient time between measurements on each analyzer to allow residual acoustic energy to attenuate to an acceptable level in each analyzer between measurements.

37. In an apparatus for ratiometric comparisons of measurements derive from the velocity of sound in fluid mixtures, the method of obtaining results which are free of instrument systematic error comprising
    employing a single sound burst oscillator and a single signal processor for all measurements obtained in a single fluid analysis instrument to render any systematic error common to all measurements,
    obtaining true time-of-flight measurements by calculating the instant in time of the on-set of sinusoidal oscillation resulting from the reception of the sound burst, the true time-of-flight being the time lapse between the on-set of transmission and the on-set of reception of the sinusoidal oscillation resulting from the sound burst, and
    utilizing a ratiometric comparative sensing technique whereby systematic errors which may be factors in the measurements appear in both numerator and denominator in the ratiometric comparison of successive measurement pairs and cancel to unity and whereby results are expressed in dimensionless numbers devoid of instrument systematic error.

38. The method of claim 37 including utilizing a detection principle and ratiometric comparative sensing technique which further provides transferability of setpoints between different fluid analyzer instruments utilizing the same ratiometric sensing technique comprising introducing the constituent fluids into separate analyzers or sequentially into the same analyzer in the apparatus, obtaining sound velocity-dependant measurements for each individual fluid, ratiometrically comparing pairs of successive measurements to obtain numerical factors, storing these numerical factors which are used to establish setpoints for monitoring deviations in fluid constituency, composition, and flow, and transferring the same to another apparatus for use in replication of fluid conditions at a remote location.

39. In an apparatus for ratiometric comparisons of measurements derived from the velocity of sound in fluid mixtures, the method for eliminating the need for recalibration of the apparatus comprising initially calibrating the apparatus response by calculating calibration factors which when arithmetically combined with the results of individual ratiometric comparisons will convert said results into common scientific or engineering units of composition, obtaining sound velocity dependent measurements of the fluid mixtures, ratiometrically comparing pairs of said measurements to obtain mathematical numbers which are dimensionless and are devoid of any systematic effects of the instrumentation utilized to obtain the measurements, and arithmetically combining these dimensionless results from the individual ratiometric comparisons with calibration factors to express results of analysis in common scientific or engineering units of composition.

* * * * *